(12) United States Patent
Bishop et al.

(10) Patent No.: US 10,039,857 B2
(45) Date of Patent: Aug. 7, 2018

(54) MINIMALLY INVASIVE TISSUE SUPPORT

(71) Applicant: Sinclair Pharmaceuticals Limited, Chester (GB)

(72) Inventors: Gordon Bishop, Santa Rosa, CA (US); Randy Lashinski, Santa Rosa, CA (US)

(73) Assignee: Sinclair Pharmaceuticals Limited, Chester (GB)

( * ) Notice: Subject to any disclaimer, the term of this patent is extended or adjusted under 35 U.S.C. 154(b) by 197 days.

(21) Appl. No.: 14/721,957

(22) Filed: May 26, 2015

(65) Prior Publication Data

US 2015/0327988 A1 Nov. 19, 2015

Related U.S. Application Data

(63) Continuation of application No. 13/609,069, filed on Sep. 10, 2012, now abandoned, which is a (Continued)

(51) Int. Cl.
*A61F 2/12* (2006.01)
*A61L 17/00* (2006.01)
(Continued)

(52) U.S. Cl.
CPC ........ *A61L 17/00* (2013.01); *A61B 17/00234* (2013.01); *A61B 17/06166* (2013.01); (Continued)

(58) Field of Classification Search
CPC ......... A61B 17/00234; A61B 17/06166; A61F 2/0059; A61F 2/0063; A61F 2/12; (Continued)

(56) References Cited

U.S. PATENT DOCUMENTS

| 4,372,293 A | 2/1983 | Vijil-Rosales |
| 4,840,629 A | 6/1989 | Bustos |

(Continued)

FOREIGN PATENT DOCUMENTS

| WO | WO 2003/086205 | 10/2003 |
| WO | WO 2003/103536 | 12/2003 |

(Continued)

OTHER PUBLICATIONS

U.S. Appl. No. 15/706,401, filed Sep. 15, 2017, Lee et al.
(Continued)

*Primary Examiner* — Tuan V Nguyen
(74) *Attorney, Agent, or Firm* — Knobbe Martens Olson & Bear LLP

(57) ABSTRACT

Embodiments of apparatus and methods for tissue lifting, or for correcting a ptosis condition caused by tissue stretching, are described. In some embodiments a tissue is supported by a support member. In some embodiments, tension is applied to a support member through at least one suspension member. The described embodiments provide examples of methods and apparatus effective for use in lifting or otherwise applying tension to various tissues, including tissues of the breast, buttock, thigh, arm, abdomen, neck and face.

19 Claims, 24 Drawing Sheets

Related U.S. Application Data continuation of application No. 13/284,832, filed on Oct. 28, 2011, now abandoned, which is a continuation of application No. 11/866,985, filed on Oct. 3, 2007, now abandoned.

(60) Provisional application No. 60/828,006, filed on Oct. 3, 2006, provisional application No. 60/933,179, filed on Jun. 4, 2007.

(51) Int. Cl.

| | |
|---|---|
| *A61F 2/00* | (2006.01) |
| *A61B 17/00* | (2006.01) |
| *A61B 17/06* | (2006.01) |
| *A61L 17/06* | (2006.01) |
| *A61L 17/14* | (2006.01) |
| *A61M 29/00* | (2006.01) |
| *A61B 90/00* | (2016.01) |

(52) U.S. Cl.
CPC .......... *A61F 2/0059* (2013.01); *A61F 2/0063* (2013.01); *A61F 2/12* (2013.01); *A61L 17/06* (2013.01); *A61L 17/145* (2013.01); *A61M 29/00* (2013.01); *A61B 2017/00411* (2013.01); *A61B 2017/00557* (2013.01); *A61B 2017/00792* (2013.01); *A61B 2017/00796* (2013.01); *A61B 2017/00867* (2013.01); *A61B 2017/00893* (2013.01); *A61B 2017/0618* (2013.01); *A61B 2017/06176* (2013.01); *A61B 2090/3908* (2016.02)

(58) Field of Classification Search
CPC ........ A61M 29/00; A61B 17/00; A61L 17/06; A61L 17/145; A61L 17/00234; A61L 17/06166

See application file for complete search history.

(56) References Cited

U.S. PATENT DOCUMENTS

| | | | |
|---|---|---|---|
| 5,451,212 A | 9/1995 | Andersen | |
| 5,584,884 A | 12/1996 | Pignataro | |
| 5,658,328 A | 8/1997 | Johnson | |
| 5,676,161 A | 10/1997 | Breiner | |
| 5,910,124 A | 6/1999 | Rubin | |
| 6,042,534 A | 3/2000 | Gellman et al. | |
| 6,110,101 A | 8/2000 | Tihon et al. | |
| 6,203,570 B1 | 3/2001 | Baeke | |
| 6,210,439 B1 | 4/2001 | Firmin et al. | |
| 6,402,585 B1 | 6/2002 | Gatto et al. | |
| 6,464,726 B1 | 10/2002 | Heljenek | |
| 6,544,167 B2 | 4/2003 | Buckberg et al. | |
| 6,595,911 B2 | 7/2003 | LoVuolo | |
| 6,638,210 B2 | 10/2003 | Berger | |
| 6,695,855 B1 | 2/2004 | Gaston | |
| 6,908,473 B2 | 6/2005 | Skiba et al. | |
| 6,960,160 B2 | 11/2005 | Browning | |
| 7,056,331 B2 | 6/2006 | Kaplan et al. | |
| 7,081,129 B2 | 7/2006 | Frank | |
| 7,081,135 B2 | 7/2006 | Smith et al. | |
| 7,326,213 B2 | 2/2008 | Benderev et al. | |
| 7,410,460 B2 | 8/2008 | Benderev | |
| 7,476,249 B2 | 1/2009 | Frank | |
| 7,601,164 B2 | 10/2009 | Wu | |
| 7,837,613 B2 | 11/2010 | Lashinski et al. | |
| 8,480,557 B2 | 7/2013 | Guterman | |
| 8,632,454 B2 | 1/2014 | Lashinski et al. | |
| 9,220,589 B2 | 12/2015 | Lashinski et al. | |
| 9,549,804 B2 | 1/2017 | Guterman | |
| 9,763,770 B2 | 9/2017 | Lee et al. | |
| 2001/0023356 A1 | 9/2001 | Shlomo | |
| 2002/0029011 A1 | 3/2002 | Dyer | |
| 2002/0143234 A1 | 10/2002 | LoVuolo | |
| 2003/0023137 A1 | 1/2003 | Gellman | |
| 2003/0191360 A1 | 10/2003 | Browning | |
| 2004/0060410 A1 | 4/2004 | Leung et al. | |
| 2004/0106847 A1 | 6/2004 | Benderev | |
| 2005/0004576 A1 | 1/2005 | Benderev | |
| 2005/0090827 A1 | 4/2005 | Gedebou | |
| 2005/0192631 A1* | 9/2005 | Grafton | A61B 17/06166 606/228 |
| 2005/0240224 A1 | 10/2005 | Wu | |
| 2005/0277806 A1 | 12/2005 | Cristalli | |
| 2006/0030939 A1 | 2/2006 | Frank | |
| 2006/0036333 A1 | 2/2006 | Smith et al. | |
| 2006/0041185 A1 | 2/2006 | Browning | |
| 2006/0069403 A1 | 3/2006 | Shalon | |
| 2006/0074314 A1 | 4/2006 | Slayton et al. | |
| 2006/0089525 A1 | 4/2006 | Mamo et al. | |
| 2006/0167338 A1* | 7/2006 | Shfaram | A61B 17/0401 600/37 |
| 2006/0201519 A1 | 9/2006 | Frazier et al. | |
| 2006/0229596 A1 | 10/2006 | Weiser et al. | |
| 2007/0005110 A1 | 1/2007 | Collier et al. | |
| 2007/0021649 A1* | 1/2007 | Nowlin | A61F 2/0045 600/30 |
| 2007/0038017 A1 | 2/2007 | Michael | |
| 2007/0055095 A1 | 3/2007 | Chu et al. | |
| 2007/0156175 A1 | 7/2007 | Weadock et al. | |
| 2008/0027486 A1 | 1/2008 | Jones et al. | |
| 2008/0082113 A1 | 4/2008 | Bishop et al. | |
| 2008/0097526 A1 | 4/2008 | Accardo | |
| 2009/0248071 A1 | 10/2009 | Saint et al. | |
| 2012/0046675 A1 | 2/2012 | Bishop et al. | |
| 2012/0232653 A1 | 9/2012 | Saint et al. | |
| 2013/0066423 A1 | 3/2013 | Bishop et al. | |
| 2013/0178699 A1 | 7/2013 | Saint et al. | |
| 2014/0046442 A1 | 2/2014 | Guterman | |
| 2015/0018946 A1 | 1/2015 | Guterman | |
| 2015/0289969 A1 | 6/2015 | Guterman | |
| 2017/0196672 A1 | 7/2017 | Guterman | |

FOREIGN PATENT DOCUMENTS

| | | |
|---|---|---|
| WO | WO 2008/042992 | 4/2008 |
| WO | WO 2009/111802 | 3/2009 |
| WO | WO 2010/051506 | 10/2009 |

OTHER PUBLICATIONS

International Search Report for PCT/US2007/080356 dated Apr. 10, 2008.

International Search Report dated Feb. 3, 2010 for PCT Application No. PCT/US2009/062879 in 10 pages.

International Search Report for PCT/US2009/036587 dated May 5, 2009.

\* cited by examiner

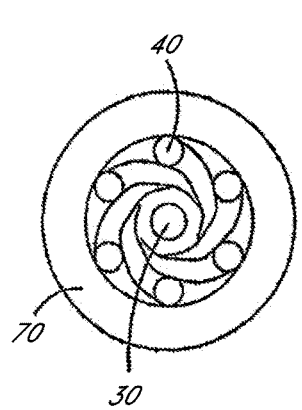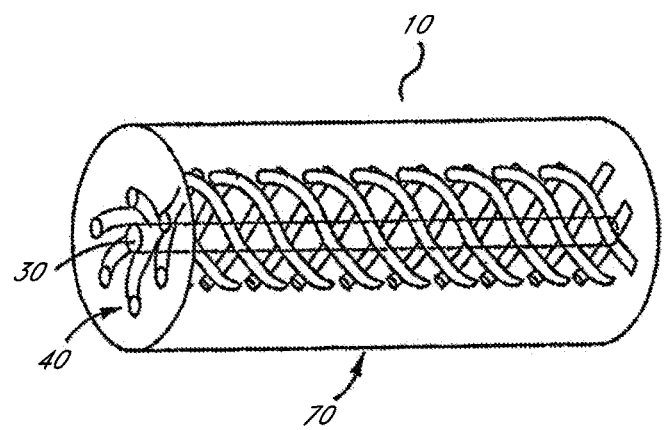
FIG. 7A  FIG. 7B
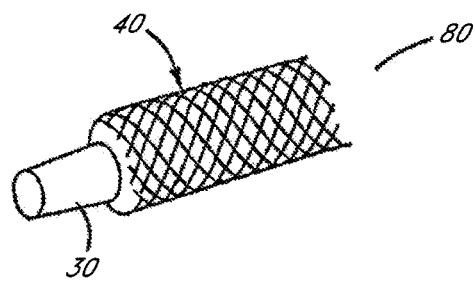
FIG. 8A
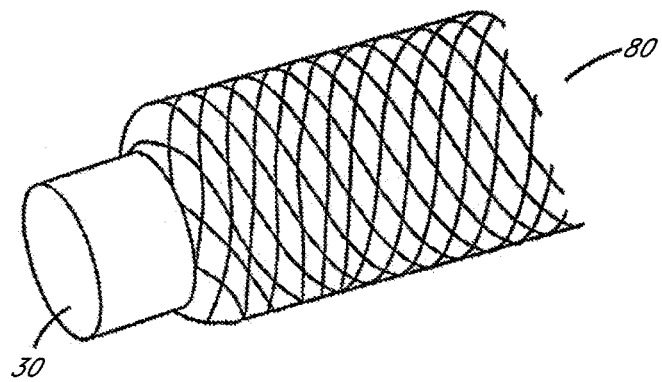
FIG. 8B

 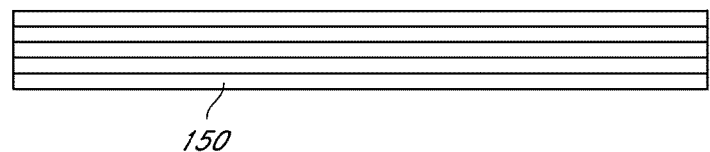
FIG. 14A    FIG. 14B
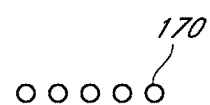 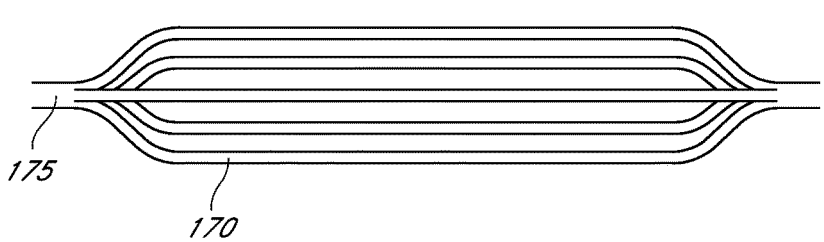
FIG. 15A    FIG. 15B

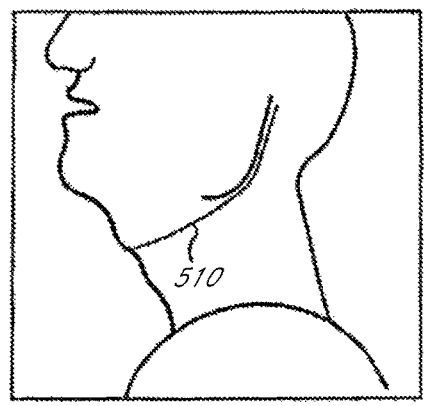 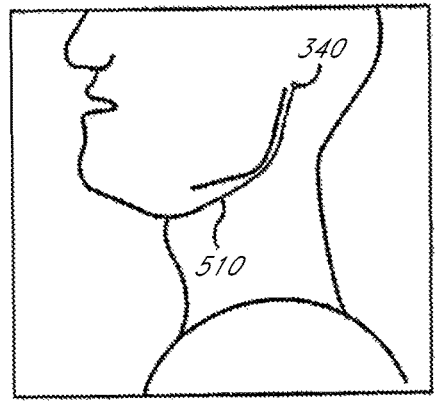
FIG. 34A     FIG. 34B
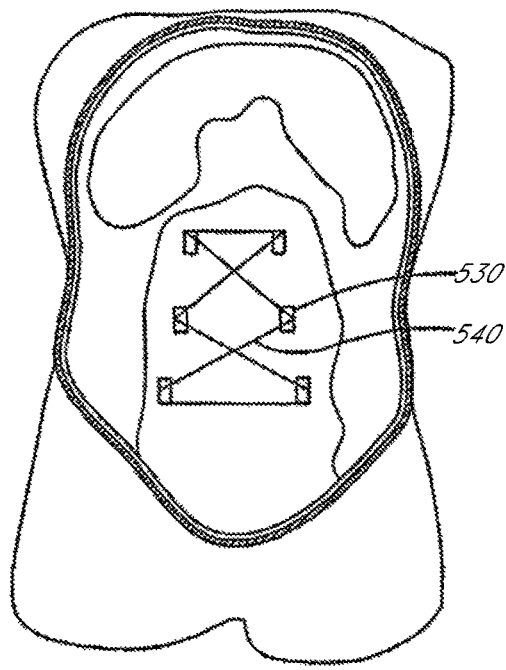
FIG. 35

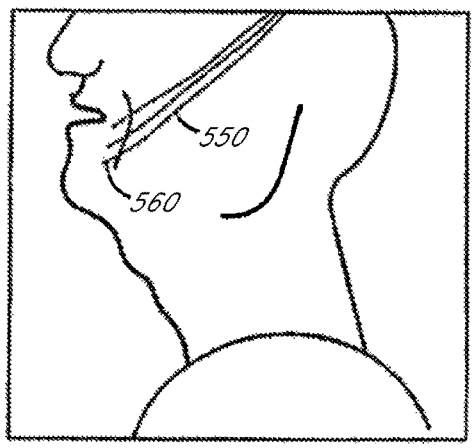 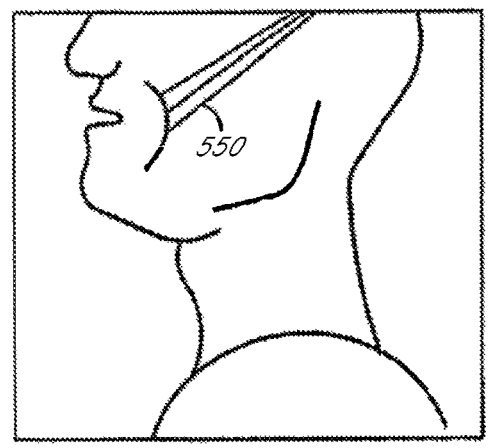
FIG. 36A
(PRIOR ART)
FIG. 36B

MINIMALLY INVASIVE TISSUE SUPPORT

CROSS-REFERENCE TO RELATED APPLICATIONS

This application claims priority under 35 U.S.C. § 120 as a continuation application of U.S. application Ser. No. 13/609,069 filed on Sep. 10, 2012, which is a continuation of U.S. application Ser. No. 13/284,832 filed Oct. 28, 2011, which is a continuation application of U.S. application Ser. No. 11/866,985 filed on Oct. 3, 2007, which is a nonprovisional application of U.S. Prov. App. Nos. 60/828,006 filed on Oct. 3, 2006 and 60/933,179 filed on Jun. 4, 2007. Each of the aforementioned priority applications are hereby incorporated by reference in their entireties.

FIELD OF THE INVENTION

Embodiments of the invention are useful in the field of minimally invasive surgical devices and methods, in particular devices and methods for use in mastopexy.

BACKGROUND OF THE INVENTION

Ptosis is a condition in a tissue or organ of the body where the tissue or organ sags, or falls, with respect to its previous position in the body. A variety of surgical and non-surgical procedures and devices have been developed to restore tissues and organs to a previous position. In particular, cosmetic surgery is frequently directed at restoring tissues to a pre-sag position.

For example, in mastopexy, mammary ptosis is corrected using a surgical procedure, without altering breast volume. In augmentation, breast volume is increased, while in reduction surgery, breast volume is decreased. Procedures can include combinations of mastopexy and augmentation or reduction procedures as well.

SUMMARY OF THE INVENTION

Embodiments as disclosed herein are directed to minimally invasive methods of tissue support.

In some embodiments, there is provided a device, for use in supporting a tissue in a patient's body, comprising; a support member, adapted to engage at least a portion of a tissue, the support member comprising a first end and a second end, the support member further comprising a plurality of support elements; and first and second suspension members, the first suspension member being coupled to the first end of the support member, the second suspension member being coupled to the second end of the support member; wherein at least one of the first and second suspension members is configured to be secured to a location in the patient's body; wherein the plurality of support elements is configured to distribute a load, from the tissue engaged by the support member, imposed on the support member; and wherein at least one of the first and second suspension members is configured to transmit a force through the support member, the force effective to move the engaged portion of the tissue from a first position to a second position.

In some embodiments, the first suspension member is coupled to each support element at a first end of each support element, and the second suspension member is coupled to each support element at a second end of each support element.

In some embodiments, the second position is superior to the first position. In some embodiments, the second position is at least one of posterior, medial, and lateral, relative to the first position. In some embodiments, the second position is posterior to the first position.

In some embodiments, each of the plurality of support elements is elongate and has a length extending along an arc, or line, that extends between the first end of the support member and the second end of the support member; wherein a first of the plurality of support elements is spaced apart from a second of the plurality of support elements along at least about 10% of a length of the first of the plurality of support elements; and wherein the length of the plurality of support elements extends from the first end of the support member to the second end of the support member.

In some embodiments, a first of the plurality of support elements is spaced apart from a second of the plurality of support elements along at least about 30% of a length of the first of the plurality of support elements; and wherein the length of the plurality of support elements extends from the first end of the support member to the second end of the support member.

In some embodiments, at least one of the support elements is fusiform shaped.

In some embodiments, at least one suspension member is configured to be secured to at least one of muscle, fascia, bone, ligament, tendon, and skin. In some embodiments, the portion of the tissue being engaged comprises at least one of breast tissue, buttock tissue, facial tissue, arm tissue, abdominal tissue, and leg tissue.

In some embodiments, each support element comprises at least one of an elongate member and a mesh.

In some embodiments, each of the plurality of support elements is coupled to a separator, effective to maintain spacing between adjacent support elements.

In some embodiments, the support member comprises an engagement member, effective to limit movement of the support member relative to the engaged portion of the tissue. In some embodiments, the engagement member comprises at least one of a barb, a hook, and a suture.

In some embodiments, at least a portion of the device comprises a biodegradable material. In some embodiments, the device further comprises a coating effective to enhance at least one of biocompatibility and healing.

In some embodiments, there is provided a device, for use in supporting a tissue in a patient's body, comprising; a support member, adapted to engage at least a portion of a tissue, the support member comprising a first end, a second end, and an inflatable portion therebetween; wherein, upon inflation, the inflatable portion is effective to increase an apparent volume of the tissue; first and second suspension members, the first suspension member being coupled to the first end of the support member, and the second suspension member being coupled to the second end of the support member; wherein at least one of the first and second suspension members is configured to be secured to a location in the patient's body; wherein the support member is configured to distribute a load imposed on the support member from the tissue engaged by the support member; and wherein at least one of the first and second suspension members is configured to transmit a force through the support member, the force effective to move the engaged portion of the tissue from a first position to a second position.

In some embodiments, the second position is superior to the first position. In some embodiments, the second position is at least one of posterior, medial, and lateral, relative to the first position.

In some embodiments, the tissue being supported comprises at least one of breast tissue, buttock tissue, facial tissue, arm tissue, abdominal tissue, and leg tissue.

In some embodiments, the inflatable portion comprises pleats. In some embodiments, the device further comprises a port for inflating the inflatable portion. In some embodiments, the port is in or on at least one of the suspension members.

In some embodiments, there is provided a device, for use in supporting tissue, comprising; a support member, adapted to engage at least a portion of a tissue, the support member comprising a first end and a second end; wherein the support member is configured to distribute a load imposed on the support member from the tissue engaged by the support member; and first and second suspension members, the first suspension member being coupled to the first end of the support member and the second suspension member being coupled to the second end of the support member; wherein at least one suspension member is configured to be secured to a location at least about 5 cm away from the engaged portion of the tissue; wherein at least one of the first suspension member, the second suspension member, and the support member comprises an elastic element; wherein at least one of the first and second suspension members is configured to transmit a force through the support member, the force effective to move the engaged portion of the tissue from a first position to a second position; and wherein the elastic element is configured to permit movement of the engaged portion of the tissue from the second position toward the first position.

In some embodiments, the second position is superior to the first position. In some embodiments, the second position is at least one of posterior, medial, and lateral, relative to the first position.

In some embodiments, the portion of the tissue being engaged comprises at least one of breast tissue, buttock tissue, facial tissue, arm tissue, abdominal tissue, and leg tissue.

In some embodiments, the elastic element comprises at least one of an elastomeric core and an elastomeric cover. In some embodiments, the elastic element comprises a spring.

In some embodiments, the at least one suspension member comprises a braided portion. In some embodiments, at least a portion of the elastic element has a nonlinear elastic constant.

In some embodiments, the device further comprises a channel member through which at least a portion of a suspension member passes, when the device is implanted in the body; wherein the channel member is configured to limit contact of surrounding tissue by the portion of the suspension member. In some embodiments, the channel member is tubular.

In some embodiments, there is provided a device, for use in supporting a tissue in a patient's body, comprising; a support member, adapted to engage at least a portion of a tissue, the support member comprising a first end and a second end; wherein the support member is configured to distribute a load imposed on the support member from the tissue engaged by the support member; first and second suspension members, the first suspension member being coupled to the first end of the support member, and the second suspension member being coupled to the second end of the support member; and a disconnect member, configured to release tension in the suspension member when a load on the device exceeds a threshold load; wherein at least one of the suspension members is configured to be secured to a location in the patient's body; and wherein at least one of the suspension members is configured to transmit a force through the support member, the force effective to move an engaged portion of the tissue of the patient from a first position to a second position.

In some embodiments, the second position is superior to the first position. In some embodiments, the second position is at least one of posterior, medial, and lateral, relative to the first position. In some embodiments, the portion of the tissue being engaged comprises at least one of breast tissue, buttock tissue, facial tissue, arm tissue, abdominal tissue, and leg tissue.

In some embodiments, the disconnect member is configured to separate a first portion of at least one of the suspension members from a second portion of the at least one of the suspension members in response to the load that exceeds the threshold. In some embodiments, the disconnect member is configured to separate at least one of the suspension members from the support member in response to the load that exceeds the threshold.

In some embodiments, there is provided a device, for use in supporting a tissue in a patient's body, comprising: an elongate suspension member, having a first end and a second end, and a length extending therebetween; wherein the suspension member is configured to engage, and exert fraction on, a tissue, resulting in the tissue moving from a first position to a second position; wherein at least a portion of suspension member is configured to shorten along the length of the suspension member in response to delivery of an energy to the suspension member; wherein the suspension member further comprises at least one engagement member, configured to engage at least a portion of the tissue; an elongate energy delivery member, coupled to at least a portion of the suspension member; wherein at least a portion of the elongate energy delivery member extends alongside at least a portion of the length of the suspension member; and wherein the elongate energy delivery member is configured to deliver the energy to the suspension member.

In some embodiments, the energy comprises at least one of electromagnetic energy, acoustic energy, and thermal energy. In some embodiments, the at least a portion of the elongate suspension member comprises collagen. In some embodiments, the at least a portion of the elongate suspension member comprises at least one of a shape memory alloy and a shape memory polymer. In some embodiments, the at least a portion of the elongate suspension member comprises a swellable material. In some embodiments, the swellable material comprises a hydrogel. In some embodiments, the at least a portion of the elongate suspension member comprises a braid.

In some embodiments, there is provided a method, for supporting a breast in a body of a patient, comprising: providing a supporting device having a first end, a second end, and a support member positioned between the first end and second end; advancing the first end of the supporting device into a breast, through a first incision that is located on one of a medial and a lateral side of the breast; withdrawing the first end of the supporting device from the breast through a second incision, located on the other of the medial and the lateral side of the breast, until the support member is positioned within breast tissue between the first incision and second incision; advancing the first end of the supporting device, from a position within the breast adjacent the second incision, to a first location, and the second end of the supporting device, from a position within the breast adjacent the first incision, to a second location; wherein both the first and second locations are superior to the first and second incisions; drawing the breast tissue toward the first and second locations; and anchoring the first and second ends of the supporting device at the first and second locations, respectively.

In some embodiments, the first and second locations are substantially the same location.

In some embodiments, the method further comprises coupling a portion of the first end to a portion of the second end, inside the body. In some embodiments, anchoring comprises coupling the first and second ends to at least one of bone, muscle, fascia, tendon, ligament, and skin.

In some embodiments, there is provided a method, for supporting a tissue in a body of a patient, comprising: placing a supporting device into the body, the supporting device comprising: a support member, adapted to engage at least a portion of a tissue, the support member comprising a first end and a second end; wherein the support member is configured to distribute a load imposed on the support member from the tissue engaged by the support member; at least one suspension member coupled to the support member; engaging the at least a portion of the tissue with the support member; applying tension to the at least one suspension member, thereby moving the engaged portion of the tissue from a first position to a second position; securing the at least one suspension member to a location in the body, such that the engaged portion of the tissue is effectively maintained in the second position; and inflating at least a portion of the supporting device to increase an apparent volume of the tissue.

In some embodiments, the portion of the tissue being engaged comprises at least one of breast tissue, buttock tissue, facial tissue, arm tissue, abdominal tissue, and leg tissue.

In some embodiments, there is provided a method, for supporting a tissue in a body of a patient, comprising: placing a supporting device into the body, the supporting device comprising: a support member, adapted to engage at least portion of a tissue, the support member comprising a first end and a second end; wherein the support member is configured to distribute a load imposed on the support member from the tissue engaged by the support member; and at least one suspension member coupled to the support member; placing the support member so as to effectively engage at least a portion of the tissue; applying tension to the at least one suspension member, thereby moving the engaged portion of the tissue from a first position to a second position; securing the at least one suspension member to a location in the body, such that the engaged portion of the tissue is effectively maintained substantially in the second position; and wherein the supporting device is configured, in response to a load that exceeds a threshold, to release tension in the at least one suspension member.

In some embodiments, the supporting device is configured to uncouple a first portion of at least one of the suspension members from a second portion of the at least one of the suspension members in response to the load that exceeds the threshold. In some embodiments, the supporting device is configured to uncouple at least one of the suspension members from the support member in response to the load that exceeds the threshold. In some embodiments, the at least one suspension member increases in length when the load exceeds the threshold.

In some embodiments, there is provided a method for use in supporting breast tissue in a patient's body, comprising: providing a support member, adapted to engage breast tissue, the support member comprising a first end and a second end; wherein the support member is configured to distribute a load imposed on the support member from the breast tissue engaged by the support member; and providing first and second suspension members, the first suspension member being coupled to the first end of the support member and the second suspension member being coupled to the second end of the support member; wherein, when implanted, the first suspension member, extends superiorly from the first end of the support member, and the second suspension member, extends superiorly from the second end of the support member; anchoring the first suspension member at a first location, and the second suspension member at a second location; wherein the first and second locations are located superiorly to the engaged breast tissue; wherein a distance between the first and second locations is greater than a greatest distance between the first and second ends of the support member.

In some embodiments, there is provided a method, for use in supporting a tissue in a patient's body, comprising: providing an elongate suspension member, having a first end and a second end, and a length extending therebetween; wherein the suspension member is configured to engage, and exert traction on, a tissue, resulting in the tissue moving from a first position to a second position; wherein at least a portion of suspension member is configured to shorten along the length of the suspension member in response to delivery of an energy to the suspension member; wherein the suspension member further comprises at least one engagement member, configured to engage at least a portion of the tissue; providing an elongate energy delivery member, coupled to at least a portion of the suspension member; wherein at least a portion of the energy delivery member extends alongside at least a portion of the length of the suspension member; and wherein the energy delivery member is configured to deliver the energy to the suspension member; delivering the energy to the energy delivery member, thereby shortening the suspension member. In some embodiments, delivering energy comprises delivering at least one of electromagnetic energy, acoustic energy, and thermal energy.

BRIEF DESCRIPTION OF THE DRAWINGS

FIG. 7A is a cross-sectional view of an embodiment of a braided suture impregnated with an elastomeric coating.

FIG. 7B is a perspective view of the suture illustrated in FIG. 7A.

FIG. 8A illustrates an embodiment of a braided suture with a hydrogel core in a pre-activation (elongated) configuration.

FIG. 8B illustrates an embodiment of a braided suture with a hydrogel core in a post-activation (shortened) configuration.

FIG. 14A is a cross-sectional view of a suture with a flat support region rolled into a circular cross-section for easy placement in the patient.

FIG. 14B is a side view of the suture shown in FIG. 14A.

FIG. 15A is a cross-sectional view of a suture with a support region comprising multiple strands that provide tissue support.

FIG. 15B is a side view of the suture shown in FIG. 15A.

FIGS. 34A-B illustrates the use of an embodiment of a suture to perform a neck lift procedure.

FIG. 35 illustrates the use of an embodiment of a suture to perform an abdominal wall tightening procedure.

FIGS. 36A-B illustrates the use of an embodiment of a suture to perform a facelift procedure.

DETAILED DESCRIPTION OF THE INVENTION

As used herein, the term "suture" is to be construed broadly. In general, the term "sutures" refers to simple suspension members, while "support system" generally refers to complex, multi-component devices that can include, without limitation, at least one support member, and associated components such as suspension members, elastic elements, safety mechanisms, and anchoring portions. A support member can comprise, in some embodiments, a plurality of support elements.

Figure 1:
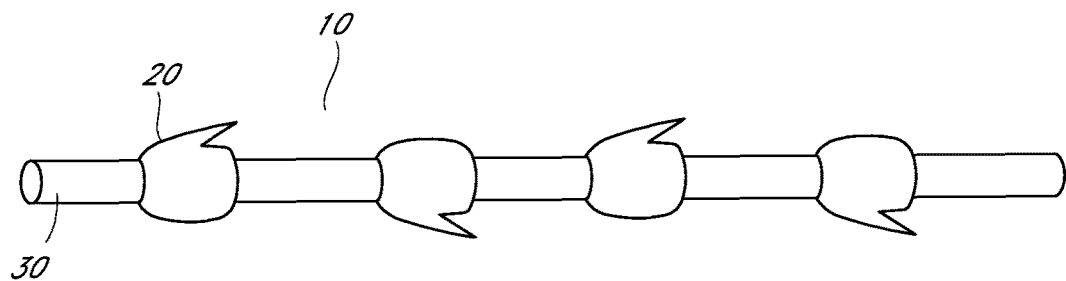
FIG. 1 illustrates an embodiment of a suture with molded barbs.

In some embodiments, a suture 10 comprising barbs 20 is provided, as shown in FIG. 1. In some embodiments, the core 30 has a relatively high tensile strength. High tensile strength can be achieved by using a polymeric material in a manufacturing process that results in a structure where the polymer chains are substantially oriented parallel to the longitudinal axis of the suture.

The core 30 of the suture 10 can be partially or completely surrounded by a like, or different material, forming the barbs 20. The properties of the suture materials can be selected on the basis of desired absorption rates, tissue in-growth, as well as a consideration of mechanical needs.

In some embodiments, the suture 10 is formed by extruding the core material to form a filament. The core 30 can then be placed in a mold that provides the barb shapes, and the mold cavity filled with material that when solid forms the outer layer of the suture, and the barbs 20.

Figure 2A:
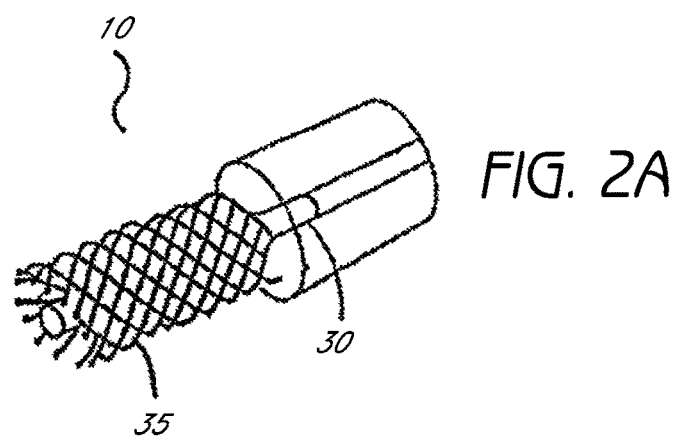
FIG. 2A illustrates an embodiment of a suture with a filamentous core and a braided portion.
Figure 2B:
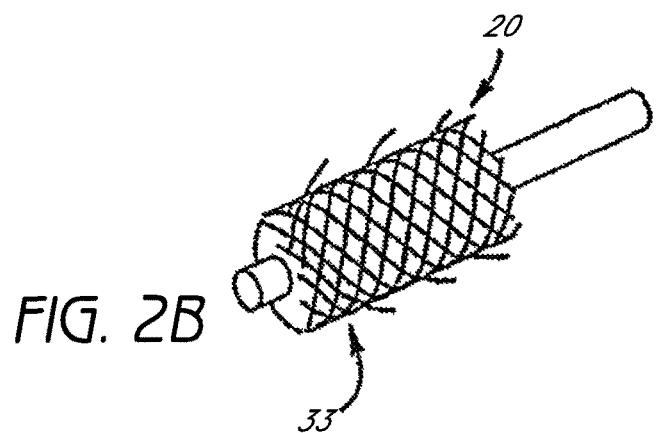
FIG. 2B illustrates an embodiment of a suture like that shown in FIG. 2A, where filaments extend outward to form barbs.

In some embodiments, the core 30 can comprise multiple filaments 33, as shown in FIG. 2A. A multiple filament design allows the suture 10 to attain a higher ratio of axial tensile strength compared to bending stiffness (i.e., resistance to bending). A portion of the filaments 33 can protrude, as shown in FIG. 2B. These protruding filaments can extend a predetermined distance, for example between about 0.2 and 2 mm. In some embodiments, the ends of the protruding filaments are configured in the shape of barbs 20. The suture can be coated with another material or can be left uncoated.

Figure 3:
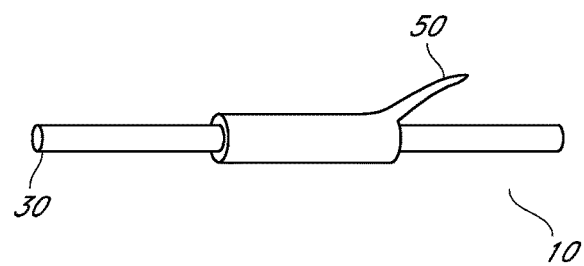
FIG. 3 illustrates an embodiment of a suture with a separately attached barb element.

In some embodiments of a suture 10, like that shown in FIG. 3, barbs 50 can be attached to the core 30 as separate members. These attached barbs 50 can be secured by bonding, gluing, or welding of the barb 50 to the outer surface of the suture core 30.

Elastic Properties

In conventional suture designs, an elastic suture typically displays only modest extensibility. Ideally, an elastic suture used in securing a healing wound should have sufficient elasticity to accommodate the swelling of tissue that occurs as part of the normal inflammatory response at the onset of healing. Additionally, the suture should continue to provide support to the tissue or wound, once inflammation and swelling have substantially subsided.

When sutures are used to support tissue, as in plastic surgery procedures, different elastic properties may be desirable. For example, during the first part of the healing process, it is possible for the sutures to pull out from the tissue in response to a modest amount of longitudinally applied force. Thus, a more elastic suture can yield enough to prevent pull-out, yet recover to its initial length, thus providing a gradual and more effective remodeling of tissue over time.

Figure 4:
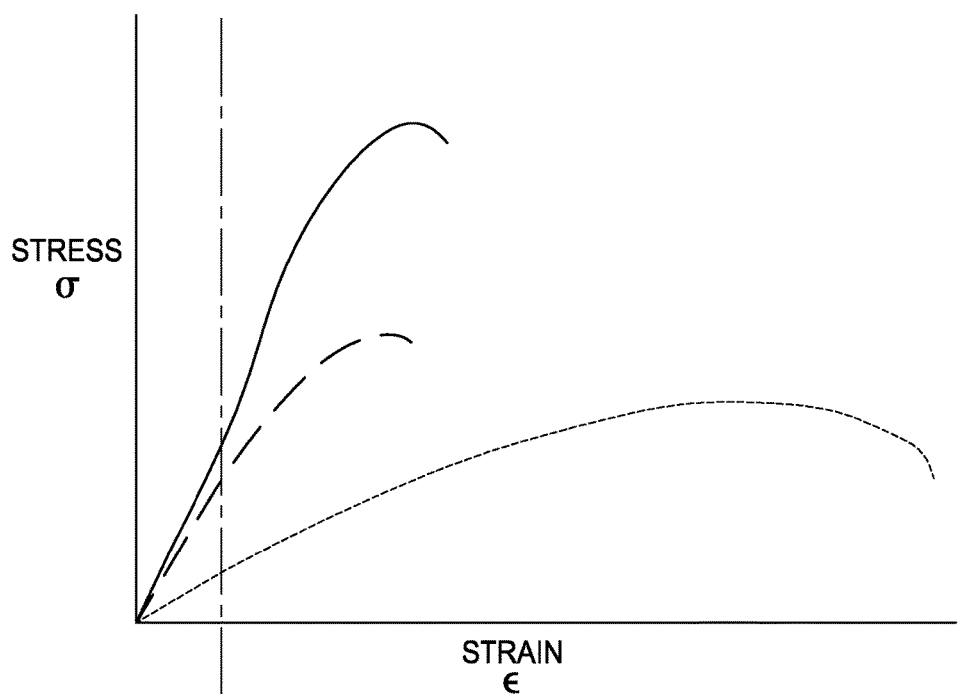
FIG. 4 illustrates the stress strain relationship among various suture types.

In some embodiments, a suture designed for use in plastic surgery procedures, for example in a facelift procedure, is capable of extending in length to 10-25%, while retaining the ability to fully recover to substantially its initial length. An example of the stress-strain curves for various types of sutures is provided in FIG. 4. Embodiments of the present disclosure (FIG. 4, dotted line), sutures are able to accommodate significant strain while displaying less stress than traditional high tensile strength sutures (FIG. 4, solid line), or even traditional elastic sutures (FIG. 4, dashed line). Thus, examples of the disclosed suture are capable of acting like a constant force spring, where force (i.e., strain) is relatively constant over a wide range of deflections.

In some embodiments, where a large mass of relatively immobile tissue is to be supported, for example in a breast lift application, it can be advantageous to provide a suture with a more progressive spring rate. In these embodiments, the stress-strain properties of the suture or support system can be optimized to simulate the natural biomechanical properties of the tissue. For example, in the case of a system for supporting the breast, the force/deflection characteristics of the support system can be designed to simulate that of Cooper's ligaments, or the combination of Cooper's ligaments and tissue that make up the outer structure of the breast.

Commonly used suture materials do not normally exhibit the properties of high elongation that are desirable in plastic surgery procedures. Natural materials, such as collagen, do however provide a highly extensible matrix that is useful in embodiments of the present disclosure. Collagen based sutures are often referred to as "gut" sutures. The source of collagen is varied and can include, without limitation, intestinal submucosa, pericardium, and tendon, from animals including humans, cow, pig, horse, donkey, kangaroo, and ostriches, etc.

Where the source of collagen is a native tissue, the tissue can be fixed in order to cross-link the collagen. Common fixatives include glutaraldehyde. Where greater extensibility is desired, chromic acid can be used as the fixative. Still other fixatives can be used, and the choice of fixative is not considered to be limiting to the scope of the present disclosure. For example, tissues can be fixed using radiation, dehydration, or heat.

In some embodiments, the suture can comprise a core made from a highly elastic synthetic polymer. Some suture materials can be made from formulations that are elastic in compression but have low strength in tension, for example hydrogel polymers. In some embodiments, the biocompatible gelling material is a solution containing water-insoluble polymers, for example non-cross-linked acrylonitrile polymers or their co-polymers, polyvinyl acetate, a linear or low-branched polymer or copolymer of 2-hydroxyethylacrylate and methyl acrylate, poly-n-vinyliminocarbonile and dimethylsulfoxide or other polar or readily water miscible solvents, for example as disclosed in U.S. Pat. No. 4,631,188 to Stoy et al., the contents of which are herein incorporated by reference in their entirety. These exemplary polymers solidify when placed in contact with living tissue as a result of absorption of water from the tissue and gradual release of the solvent into the surrounding tissue.

In obtaining copolymers, use can be made of additional monomers, such as acrylamide (including N-substituted), acryl hydrazide (including N-substituted), acrylic acid and acrylates, glutarimide and vinyl sulfone. Solvents can include glycerol and its mono- or diacetates, methanol, ethanol, propanol and iso-propanol, dimethylformamide, glycols, and other suitable solvents.

Figure 5A:
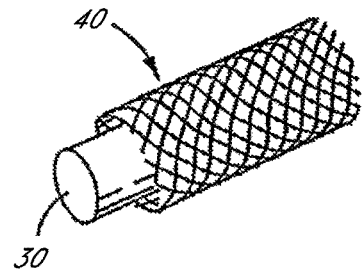
FIG. 5A illustrates an embodiment of a braided suture.
Figure 5B:
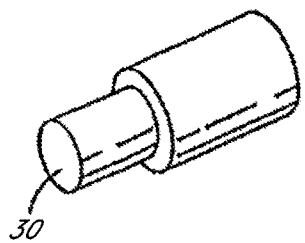
FIG. 5B illustrates an embodiment of the suture shown in FIG. 5A, with the braided portion removed to reveal the core.

In some embodiments, the core 30 can be covered with a braided portion 40 as shown in FIG. 5A. The braid can be made from traditional high tensile strength suture materials. Here, the angle of the braid can be selected such that the braided structure can elongate from its free state. Elongating the braid results in a decrease in the diameter of the lumen of the braid, and in turn results in compression of the core 30, which in turn resists further deformation of he braid. An embodiments of a suture core with the braid 40 relaxed is shown in FIG. 5B. As indcted above, in embodiments employing a hydrogel polymer core, the core material will be weak in tension, but will effectively resist compression.

Figure 6A:
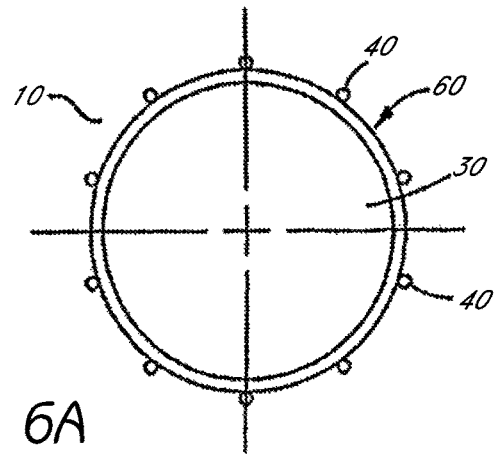
FIG. 6A is a cross-sectional view of an embodiment of a braided suture that includes a membrane lying between the braid and the suture core.
Figure 6B:
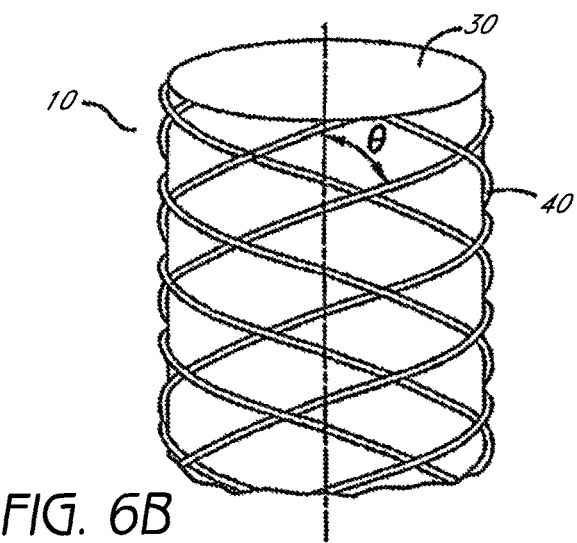
FIG. 6B is a side view of the suture illustrated in FIG. 6A.

In some embodiments, the core 30 can be separated from the braided portion 40 by a membrane 60 that prevents the individual braid filaments from cutting into the core material, as shown in FIG. 6A and B. Again the angle of the braids, relative to the longitudinal axis of the core (θ in FIG. 6B), can be selected such that the braid can be elongated.

In some embodiments of a highly elastic suture, the suture includes a core 30, a braided portion, 40, all of which is impregnated with an elastomer 70. In some embodiments the elastomeric portion can comprise a "core" of one or more components the device. In some embodiments, an elastomeric material can be used to cover device components. In some embodiments, an elastomeric material can cover other portions of the device, providing an "elastomeric cover." For example, during manufacture, the suture can be forced into a foreshortened configuration and then impregnated with an elastomeric coating. The elastomer 70 can substantially impregnate the weave of the braid 40 and is effective to behave mechanically like an additional "core." The elastomer is also effective to provide resistance to elongation. Neither the composition of the elastomer, nor methods of coupling or applying it to other components of the suture are limiting. Conveniently, in some embodiments, the elastomer can comprise without limitation, silicone, thermoset polyurethane, glycolide-co-caprolactone, copolymers of lactic acid and sebacic acid, and the like, as well as combinations of more than one elastomeric material.

Shrinkable Sutures

In some surgical applications, an advantage is provided by embodiments that are able to gradually shrink in length over time, or which can be made to shrink at a later time, in response to an activation provided by a physician.

In some embodiments, a shrinkable suture 80 comprises a core 30 surrounded with a filamentous braid, as shown in FIG. 8A. Here the angle of the braid is such that as the core is allowed to expand in diameter it applies a force to the braid which shortens in length as a result, as shown in FIG. 8B. Shortening of the braided portion results in an overall shortening of the entire suture. The core material can comprise a hydrogel or other suitable swellable material.

Shrinkable Sutures

In some embodiments, a shrinkable suture comprises a bioabsorbable core, surrounded by a shape memory or other form of bias member. When placed in the patient, the bioabsorbable core 35 is absorbed over time. As the bioabsorbable core is absorbed it will weaken, with the result being that the force generated by the bias member, will dominate the biomechanical property of the suture.

Figure 9:
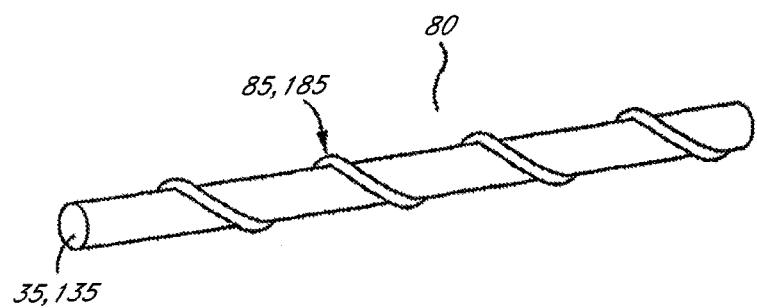
FIG. 9 illustrates an embodiment of a suture in which shortening of the suture is provided by a shape memory material.

In some embodiments, an example of which is shown in FIG. 9, the shrinkable suture 80 is configured to shrink in response to an activation energy or signal. in one case, a shrinkable suture comprises a shrinkable core 35 that heals into the tissue into which the suture is placed. In some embodiments, the shrinkable core 35 comprises collagen. The shrinkable suture 80 further comprises a energy transfer member 85 for delivering energy to the shrinkable core 35. In some embodiments, the energy transfer member 85 comprises a wire that can be heated by RF energy, or via a directly applied electrical current. Upon heating, the wire transfers energy to the shrinkable core 35, which in turn results in heating of the shrinkable core 35. In response to the thermal energy, the shrinkable core 35 in turn shrinks, creating tension in the tissue into which the shrinkable suture 80 is embedded. In the case of a shrinkable core comprised of an unfixed tissue, a temperature of 42° C. can be effective to result in shrinkage. In some applications it can also be desirable to cool the tissue immediately after the heat shrinkage step in order to minimize damage to surrounding tissue.

In some embodiments of a shrinkable suture, the suture comprises a first material 185 having a relaxed length and a deformed length, where the deformed length is longer that the relaxed length. In some cases the deformed length is 10-30% greater than the relaxed length. In some embodiments, the suture is extended to its deformed length, and that configuration held by a second material 135 that resists relaxation. Conveniently, the second material 135 can be biodegradable, such that when the suture is placed in the body, the second material is absorbed over time. Once enough of the second material has been absorbed, the first material 185 assumes its relaxed length, and the suture shortens.

In some embodiments, the first material can comprise Nitinol or any other suitably elastic material, as shown in FIG. 9. In some embodiments the first material 185 can comprise a shape memory material, that can be activated after a period of time to assume a memorized length, that results in shortening of the suture, or an increase in tension imparted by the suture on the surrounding tissue. Activation can be performed after a period of time sufficient for the second material 135 to be absorbed by the body.

Tissue Ingrowth

Healing typically occurs in three stages: inflammation, tissue formation, and matrix formation and remodeling. Matrix formation and remodeling can persist for as long as 6-12 months after wounding. Sutures used for temporarily holding tissues together are generally designed to minimize inflammation. Sutures designed to support tissue, such as those used in plastic surgery lift procedures, should also encourage tissue ingrowth, so that eventually the suture is further supported by a column of native collagen-containing scar tissue.

A variety of methods can be used to promote tissue ingrowth. When sutures made from naturally occurring material are used, this can include, methods of fixation of the suture material(s). For example, glutaraldehyde, EDC or epoxy fixatives result in sutures with more tissue ingrowth potential than do other fixatives. Where synthetic suture materials are used, braiding can be used to enhance tissue ingrowth. In some cases, synthetic materials can be manufactured such that they are porous. Implants with porosity greater than about 50 to 75 μm will generally permit tissue infiltration and vascularization. Porosity can be varied the construction of the suture, for example by providing a multifilament suture with a loose braid, or with twisted filaments.

Absorbability

All embodiments described herein can be fashioned from bioabsorbable materials. Materials can include those from natural sources such as gut, and other like materials, or synthetic materials. A variety of polymers can be used to produce bioabsorbable sutures including, without limitation, poly(glycolic acid), poly(glactin), poly(para-dioxanone), poly(trimethylenecarbonate), or poly(caprolactone). Different combinations of materials can be used to produce sutures that display different rates of absorption in vivo. In some embodiments, sutures can comprise both absorbable and non-absorbable materials.

Preventing "Cheese-Wire" Effect

For supporting tissues, especially larger masses of tissue, such as the breast or buttocks, some embodiments can be designed to prevent what is known as the "cheese-wire" effect; i.e., cutting through tissue by the suture or support member due to movement of the suture or support relative to the adjacent tissue. Cheese-wiring is particularly evident when using very thin sutures, or ones with abrasive surfaces.

In some embodiments, using a suture made from a natural material can be effective to reduce the cheese-wire effect, due to their relatively large cross section and smooth surface, and because they better heal into the surrounding tissue.

Figures 10A, 10B:
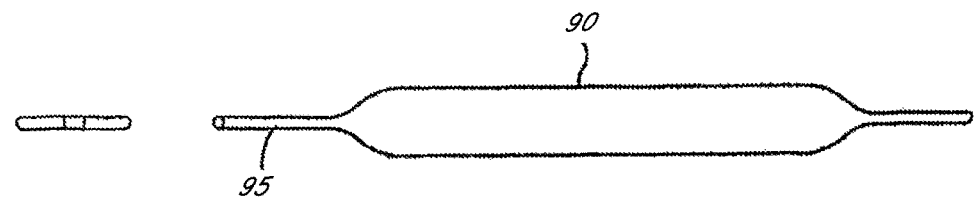
FIG. 10A is a cross-sectional view of an embodiment of a suture having a widened portion to spread out loading and limit cheese wiring of the suture through tissue.
FIG. 10B is a side view of the suture shown in FIG. 10A.

In some embodiments, a suture or a support system can comprise a region with a wide cross section 90 in at least one direction, as shown in FIG. 10A and B. Thinner ends 95 can be provided to improve ease of securing the suture in place in the patient. In some embodiments, the suture can be configured as a thin-walled tube, analogous to an angioplasty balloon.

Figure 11A:
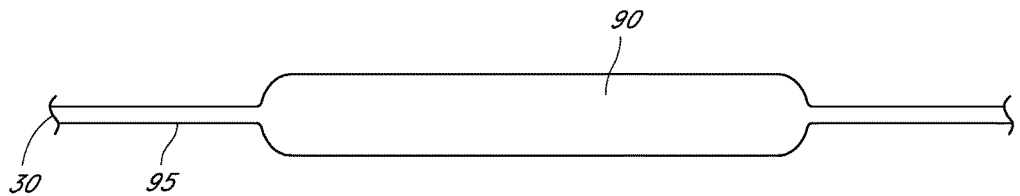
FIG. 11A illustrates side view of an embodiment of a suture having a widened portion to spread out loading in an extended conformation, where the widened portion is expandable.
Figure 11B:
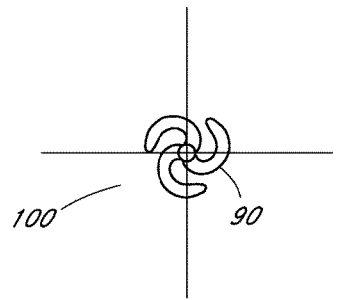
FIG. 11B illustrates a suture like that shown in FIG. 11A that has been rolled up for delivery.
Figure 11C:
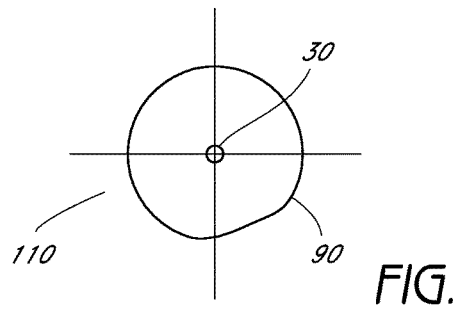
FIG. 11C illustrates an end view of suture like that shown in FIG. 11A that has been expanded.
Figure 11D:
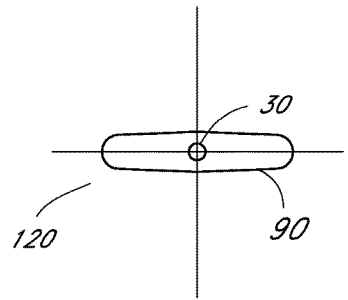
FIG. 11D illustrates an end view of a suture like that shown in FIG. 11A that has been expanded and then flattened.

The suture can be folded down into other configurations. For example, a folded suture 100 can be produced by drawing the unfolded suture, shown in FIG. 11A, through a folding die, as in FIG. 11B. Once the suture is placed in a desired position, it can be configured to assume a shape that provides a wider support area effective to support tissue, while limiting the extent to which the suture will cut into the tissue. In one method, the folded suture 100 shown in FIG. 11B is expanded to form an inflated or expanded suture 110, shown in FIG. 11C, which is then deflated in order to provide a flattened suture 120, shown in FIG. 11D.

Figure 12A:
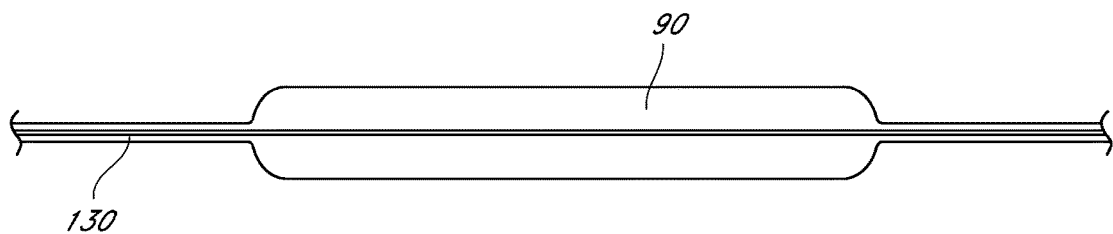
FIG. 12A illustrates side view of an embodiment of a suture having a widened portion, and further comprising support members.

The suture can optionally include supports 130 running either internally or externally, to provide additional tensile strength, as shown in FIG. 12A. In some embodiments, the supports comprise wires running along the longitudinal axis of the suture. Other supporting elements other than wires can also be used.

Figure 12B:
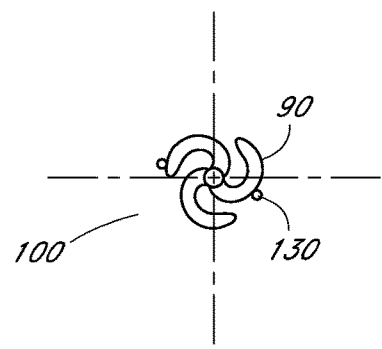
FIG. 12B illustrates a suture like that shown in FIG. 12 that has been rolled up for delivery.
Figure 12C:
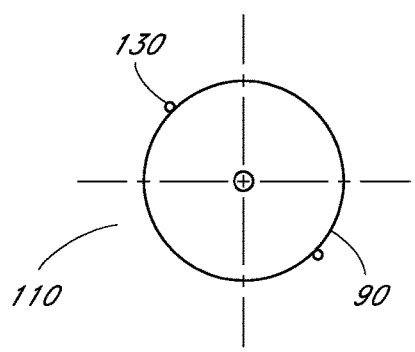
FIG. 12C illustrates a cross-sectional view of a suture like that shown in FIG. 12 that has been expanded.
Figure 12D:
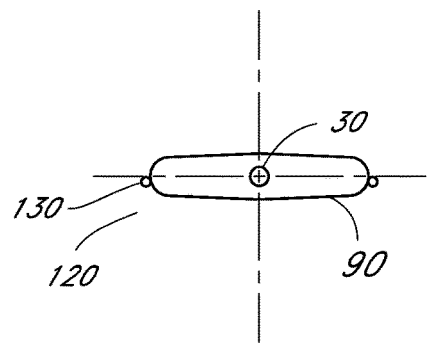
FIG. 12D illustrates an end view suture like that shown in FIG. 11A that has been expanded and then flattened.

A suture with supports 130 can be reconfigured as described above. For example, as with the suture shown in FIG. 11, a portion of a supported suture can comprise an inflatable region. As above, the suture 90 can be folded 100, by drawing through a folding die, as in FIG. 12B. The folded suture can be expanded 110, as in FIG. 12C, and then flattened 120, as in FIG. 12D.

In some embodiments, the device can be inflated with an inflation media. In some embodiments, the inflation media can be removed and the device deflated, or the inflation media can remain, in which case the device remains inflated. In some embodiments, the device can be inflated with a fluid (i.e., gas or liquid) that later changes viscosity, converts to a gel, or solidifies. In some embodiments, the device can be expanded mechanically by use of a dilation tool. The dilation tool, in some embodiments, comprises a wire or plurality of wires that can also be used to form the device into the flattened configuration 120.

Figure 13A:
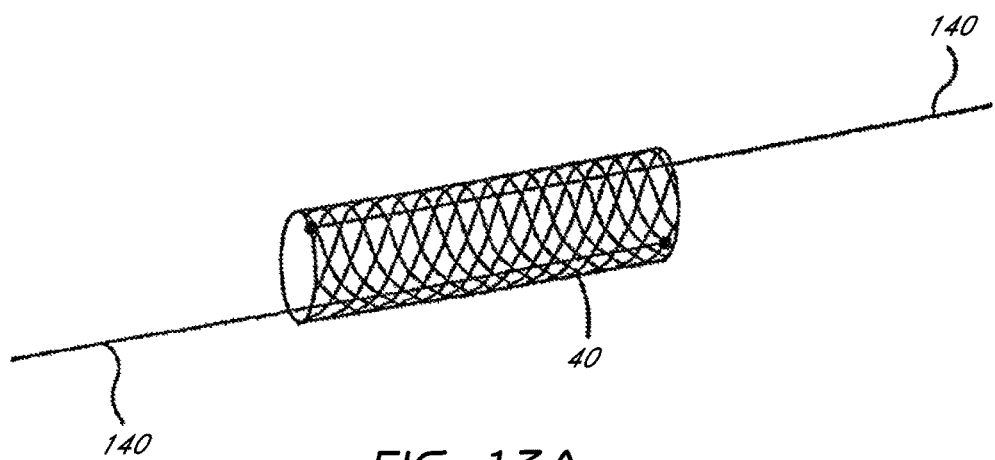
FIG. 13A illustrates a perspective view of a suture with a braided region that shortens and widens when attached sutures are placed under tension, in an extended conformation.
Figure 13B:
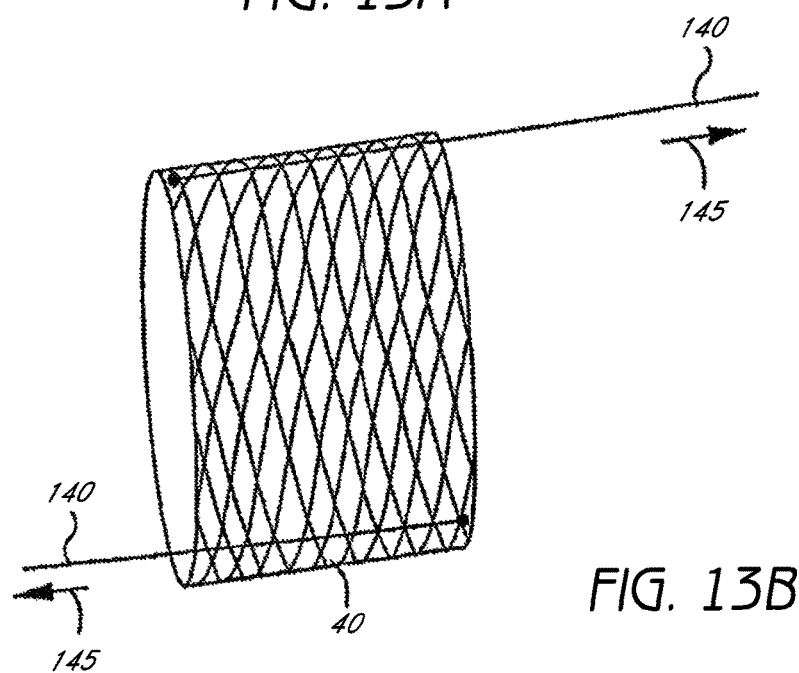
FIG. 13B illustrates a perspective view of a suture like that shown in FIG. 13A in the shortened conformation.

In some embodiments, wires 140 are connected to opposite ends, of a braided section 40, as shown in FIG. 13. Tensioning 145 of the wires will result in shortening and widening of the braided region, resulting in a wider support area.

In some embodiments, an expandable suture can be fashioned from a small-diameter, expandable tube. In some embodiments, a second suture passes through the lumen of the tubular suture, and is attached to a plug having a significantly larger diameter than the inner diameter of the tubular suture. Once the tubular suture is in place in the patient, the plug is drawn through the tubular suture, resulting in expansion of the tubular suture diameter. In some embodiments, the tubular suture diameter can be expanded by 500%. By optimizing the wall thickness of the tubular suture, the suture once expanded, will tend to assume a flattened configuration.

In some embodiments, a suture can be expanded with a heated fluid. Increasing the temperature of the suture can provide several advantages, including, and without limitation, allowing easier expansion of the suture, accelerating tissue-ingrowth, and inducing shrinkage of collagen in the region surrounding the suture.

In some embodiments, a suture 150 is provided as a flat strip of material, which can then be rolled up into a smaller diameter for easier insertion into the patient, as shown in FIG. 14A and B. After insertion, the suture can be unrolled back to the flattened configuration to provide more effective tissue support. In some embodiments, at least the flat portion of the suture comprises a shape memory material, such that it spontaneously assumes a flattened configuration upon release from a delivery device, for example a sheath, specialized needle, or trocar.

In some embodiments, a suture can comprise a plurality of wires 170 coupled to either an anchor point, or a gathering point 175 short of an anchor point, as shown in FIG. 15. Providing a multiplicity of wires effectively spread out the weight of the tissue being support, thereby reducing the tendency for a single wire to cut into tissue.

Figure 16A:
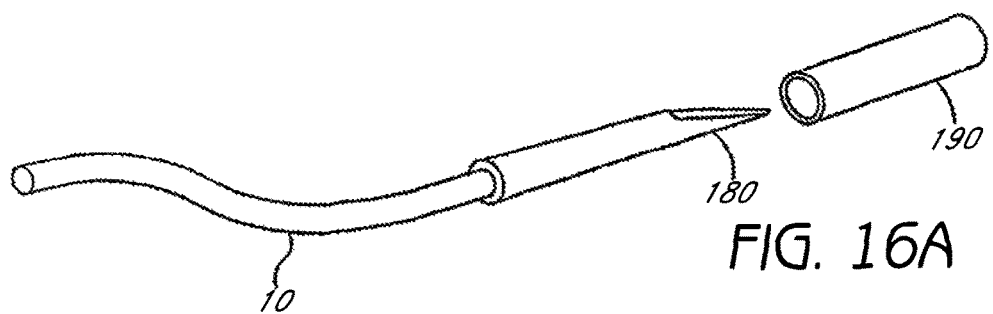
FIG. 16A illustrates a needle and sheath arrangement for use in delivering a suture.
Figure 16B:
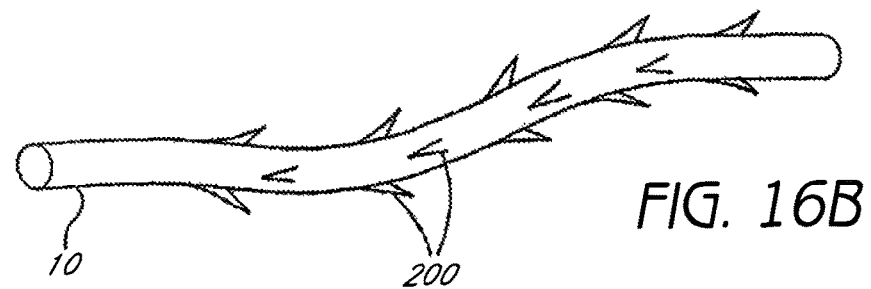
FIG. 16B illustrates a suture having bidirectionally oriented barbs.

In delivering embodiments of a suture as described herein, the suture 10 can be provided attached to a needle 180, or inserted inside a protective delivery sheath 190, as shown in FIG. 16A. Delivery of a barbed suture inside a trocar, sheath, or catheter, for example, allows efficient delivery of the suture regardless of the orientation of barbs. In some designs, delivery of barbed sutures by needle required that the barbs be oriented such that the suture can glide into the tissue into which it is inserted (i.e., the barbs face away from the direction of insertion). These designs also require that the skin be punctured a second time in order to access the implanted needle, so that it can be trimmed from the suture and removed following suture placement.

In embodiments of the present disclosure where the suture can be delivered within a trocar or sheath, some techniques permit delivery of the suture with only a single skin puncture. This can reduce the risk of complications due to infection, reduce the amount of pain involved in a procedure, and allow for more rapid recovery of the patient. In addition, use of a the delivery sheath can prevent engagement of the tissue by the barbs until the sheath is removed, as so sutures with bidirectionally oriented barbs 200 can be easily delivered.

For example, with current sutures, performing a facelift procedure requires sutures enter near the hair line and exit through the cheek near the nasolabial fold. After the procedure, the patient is left with sutures that protrude from the face, which is aesthetically unappealing. In response, the suture ends are trimmed such that they lie just below the surface of the skin. In some case, however, the ends can erode through and reappear on above the surface of the skin. Trocar or sheath delivery avoids these problems.

Figure 16C:
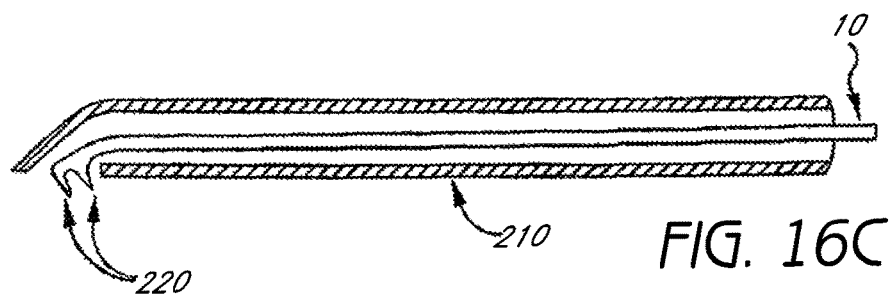
FIG. 16C illustrates a sheathed suture with barbs to engage tissue to assist in deployment.
Figure 16D:
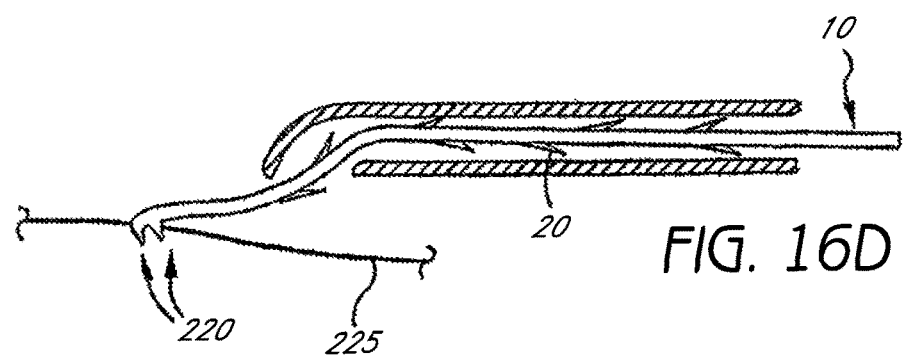
FIG. 16D illustrates the suture of FIG. 16C with an end extended from the sheath as during deployment.

In some embodiments, one of which is shown in FIG. 16C, a delivery sheath 210 for a suture 10 includes a small opening through which a portion of the suture can protrude. A region at or near the tip of the suture can comprise a barbed end 220. During placement of the suture, the suture can be substantially fully enclosed within the sheath, such that the barbs do not grasp tissue while the sheath and suture are being advanced, as shown in FIG. 16C. After the suture end is in a desired location, the barbed end 220 of the suture 10 can be advanced out of the sheath 210, allowing the barbs to engage adjacent tissue 225. Once engaged, the barbs will effectively anchor the end of the suture substantially in place, while the sheath is withdrawn, exposing the remainder of the suture, as shown in FIG. 16D. The suture can include additional barbs 20 in addition to those located at or near the end, to further anchor the suture in place once the delivery sheath has been removed.

Figure 16E:
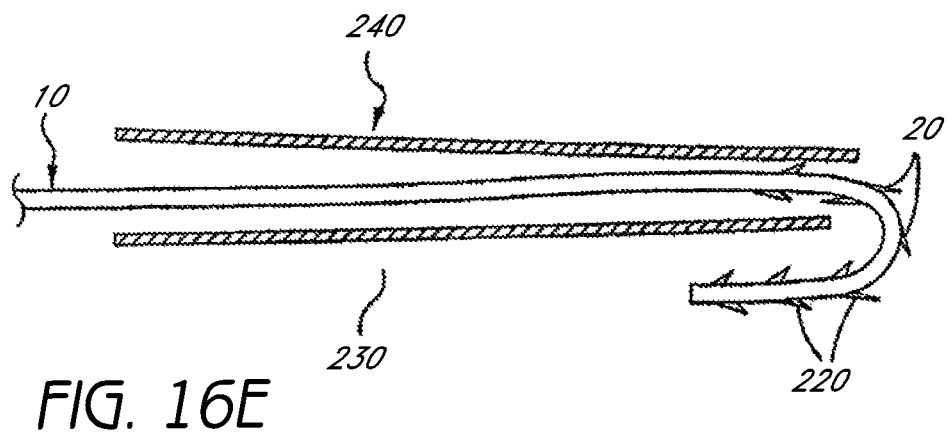
FIG. 16E illustrates an embodiment of a sheathed suture and deployment sheath where the end of the suture can be bent backwards as part of the method of deployment.

In some embodiments, a trocar 240 that is open at both ends 240 can be provided to deliver the suture 10. A barbed suture can be passed through the trocar, the barbs oriented so that the suture, once exposed to adjacent tissue, resists movement relative to the trocar. In some embodiments, a length of the barbed suture extends out from the end of the trocar, as shown in FIG. 16E. The length of suture extending from the suture can be from about 0.5 cm to about 5 cm, although this is not considered limiting. Pushing on the trocar results in the exposed portion of the suture doubling back on itself, such that the barbs will engage the adjacent tissue, as shown in FIG. 16E. Once the end of the suture is set in place, the trocar can be withdrawn, leaving the suture in place. Tensioning can be performed in a similar manner as that used with other barbed suture embodiments described herein.

The distal end of the trocar can be cut at an angle or ground such that the end of the trocar forms a point, while providing room for bending of the suture. In an exemplary embodiment, a trocar has a 0.5 mm OD and a 0.3 mm ID, and is about 225 mm long. A suture of slightly less than 0.3 mm diameter fits easily within the trocar.

Figure 16F:
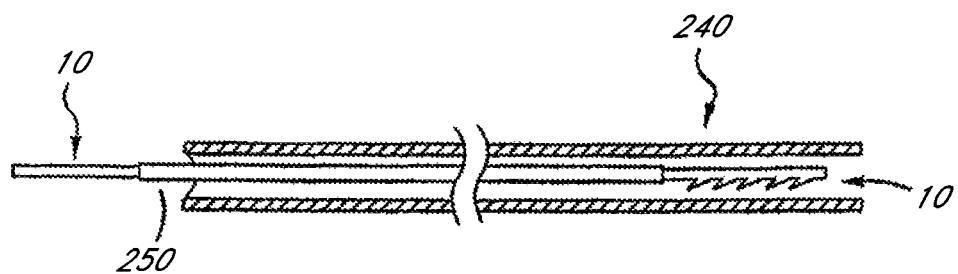
FIG. 16F illustrates an embodiment of a sheathed suture where deployment is aided by a pushable tube.

In some embodiments, coaxial arrangement of a support material surrounding the suture can be used to improve pushability of the suture, as shown in FIG. 16F. The support member 250 can be coupled to the proximal end of the suture to aid in delivering the suture with a pushing force. After delivery, cutting the end of the suture distal of the coupling would release the support from the suture, and allow withdrawal of the support and trocar, leaving the suture in place. The support member can be made from a variety of materials including, without limitation, Nitinol, surgical steel, or polymers such as PEEK, polyimide, polyethylene, polypropylene, or composite material suitable for use in medical devices such as catheters.

In some embodiments, the delivery system includes a multi-part needle, as shown in FIG. 17A-D. In some embodiments, the needle has two components, a needle 260 having a first radius of curvature, and a hypodermic tube 270 having a second radius of curvature. The first radius will be greater than the second radius. For example, the first radius of curvature of the needle can be 5 cm, while the radius of curvature of the tube can be 15 cm. The needle and tube are coaxially arranged such that the needle is slidably held within the tube.

Figure 17A:
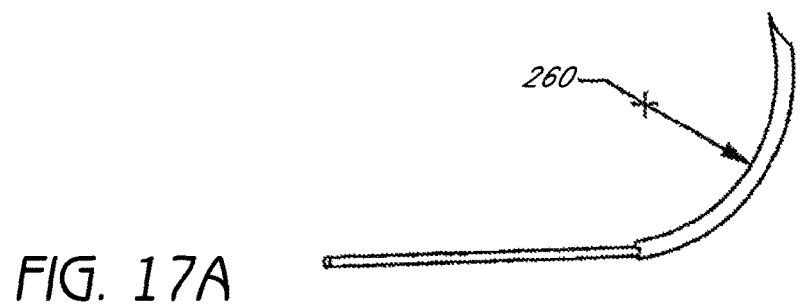
FIG. 17A illustrates an embodiment of a curved needle for use in deploying a suture along a curved path.
Figure 17B:
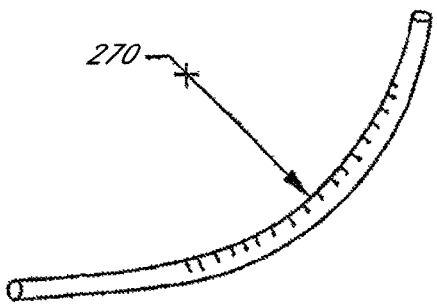
FIG. 17B illustrates a tube configured to hold a needle, and which has a larger radius of curvature than the needle of FIG. 17A.
Figure 17C:
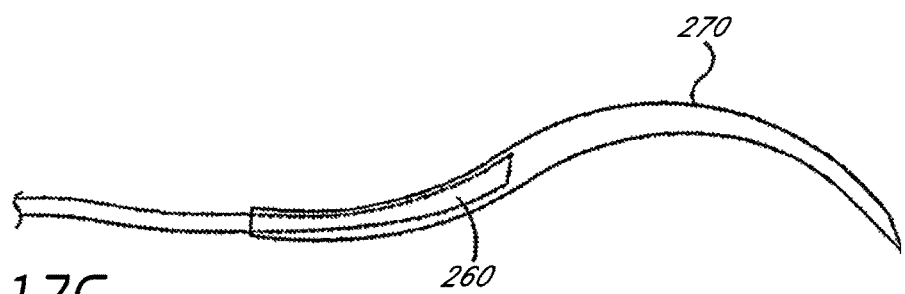
FIG. 17C illustrates a coaxial needle combination where the tip of the inner needle is pulled back from the end of the outer needle.
Figure 17D:
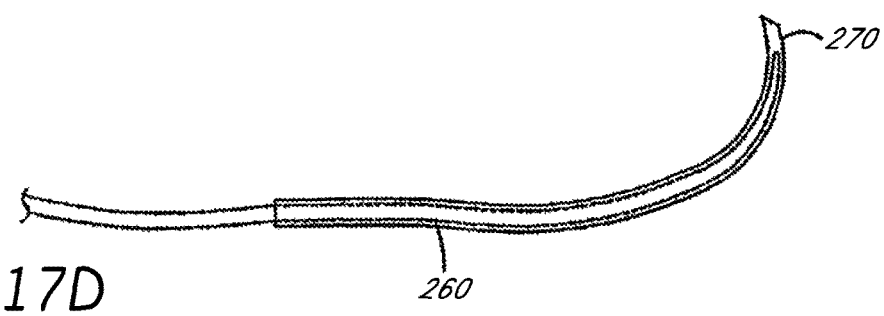
FIG. 17D illustrates a coaxial needle combination where the tip of the inner needle is inserted nearly to the end of the outer needle.

In using this system, the surgeon can continually alter the path of the suture by simply regulating how much of the needle 260 is held within the hypodermic tube 270. Where less of the needle is within the tube, the radius of curvature will be dominated by the shape of the tube and have, in this example a radius of 15 cm. Where more of the needle is within the tube, the needle will force the tube to take on a shape with a smaller radius, and thus follow a track of smaller radius, for example a radius of 5 cm. Thus, the surgeon can advance a suture over a more or less curved path, as shown in FIG. 17C and D.

It will be readily understood that the radii recited above are provided only as examples, and various combinations of needles and tubes with varying radii can be used. In addition, the system can include a needle and a plurality of tubes, such that the device could be telescoped in order to provide even finer control of the suture path through tissue.

Coaxial, multiaxial, steerable designs can also be applied to the trocars and catheters as described above. In addition, the systems can also include guide wires that the trocar or catheter passes over. Guide wires can include a needle tip and be steerable, providing an even smaller radius pathway through tissue.

To aid the physician in placing sutures, the suture can include identifiers to mark barbed regions, or the length of the. suture contained within a trocar, for example. In one embodiment, the suture is color coded with a particular color indicating a barbed region, while a different color can be used to indicate a non-barbed region. In some embodiments, other colors or marking can be used to indicate regions with distinctive mechanical properties. For example, and without being limiting, a third color can be used to indicate a region of increased elasticity.

During the surgical procedure, visualization can be accomplished by direct or indirect methods, including ultrasound, MRI, CT, or using an endoscopic tool and camera combination, among other imaging modalities. Sutures, needles, and trocars, can include markers as are known in the art for visualization when using radiographic imaging modalities. Such markers can be made, without limitation, from metals such as gold, platinum, stainless steel, and other suitable metallic alloys or even non-metallic materials. Such markers can be included during the manufacturing process.

An advantage provided by some suture embodiments, as described herein, is the ability to adjust or re-tension the suture after placement. Adjustment permits the surgeon to maintain a particular tissue configuration and appearance over time. In some cases, such as where the suture does not include barbs, or where the suture does not protrude through the skin and is therefore relatively inaccessible, an additional adjustment mechanism can be included with the suture, in order to provide a way in which to vary tension of the suture during the course of the healing process, and even afterward.

In some embodiments, the adjustment mechanism comprises a knot and a ratchet mechanism. In some embodiments, the adjustment mechanism can comprise a tang in a groove, analogous to a zip tie device. Where possible, embodiments comprising a knot are designed to be lowprofile, such that the adjuster does not produce a bump, or erode through the skin.

Figure 18:
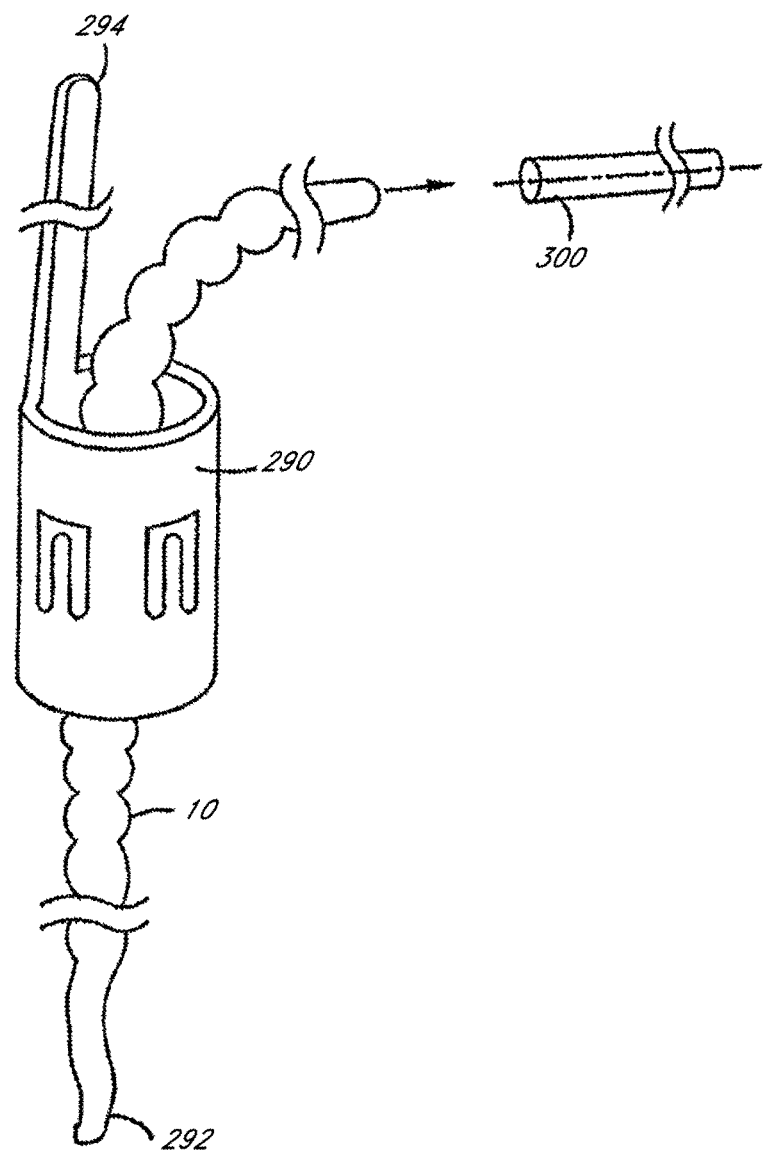
FIG. 18 illustrates an embodiment of a device for deploying and tensioning a suture, as well as for connecting suture ends.

In some embodiments, the ends of a single suture, or the ends of two separate sutures, can be joined by a linking device, where a first end is a tube 290, and a second end has a substantially round cross-section 300, as shown in FIG. 18. The second end is inserted into the tubular section of the first end. A skived area near the first end allows the second end to protrude.

A variety of methods of securing the first and second ends can be used. In some embodiments the ends can be secured by an adhesive that is cured in response to heat, pressure, moisture, or a chemical catalyst. In some embodiments, the tubular section can be made to be shrinkable, or alternatively be made from a shape memory material. In some embodiments, the second ends include barbs that engage the first end, or a feature on the first end such as a pocket. In some embodiments the barbs can be on the first end, in the lumen of the tubular portion, and engage the second end which can be barbed or not. The second end can further comprise a textured surface, or multiple regions of varying diameter to better engage the first end. In some embodiments, a tubular section engages two separate sutures having substantially round cross sections. In some embodiments, the tubular connector section can be deformable, and will adapt to the cross-sectional shapes of the sutures to be joined. Conveniently, the tubular member 290 can include an anchor 294, for securing the joining device in place in the patient. A suture end can also include an anchor 292.

A number of embodiments of the present disclosure are compatible for use in performing breast lift procedures. In some embodiments, the support member can be composed of Proline™, a non-elastic polymer line. The support member can be placed underneath the breast tissue, and secured by means of a knot or a fastener to a body landmark such as a tendon, bone, or the like. As described above, the system can include suspension members that are either elastic or non-elastic. The system can further include a safety disconnect, permitting the suspension members to release when under an increased load, in order to prevent damage to the breast tissue by the support system.

Use in Breast Procedures

Figure 19:
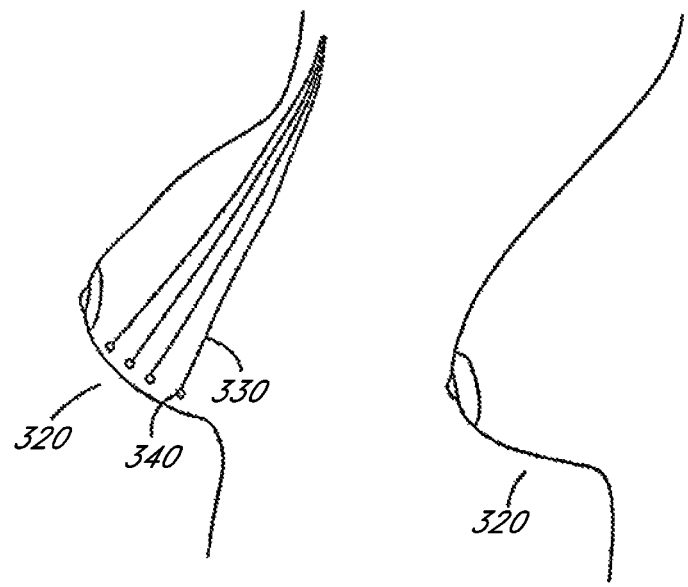
FIG. 19 is a side view illustrating a placement of sutures to perform a breast lifting procedure.
Figure 20:
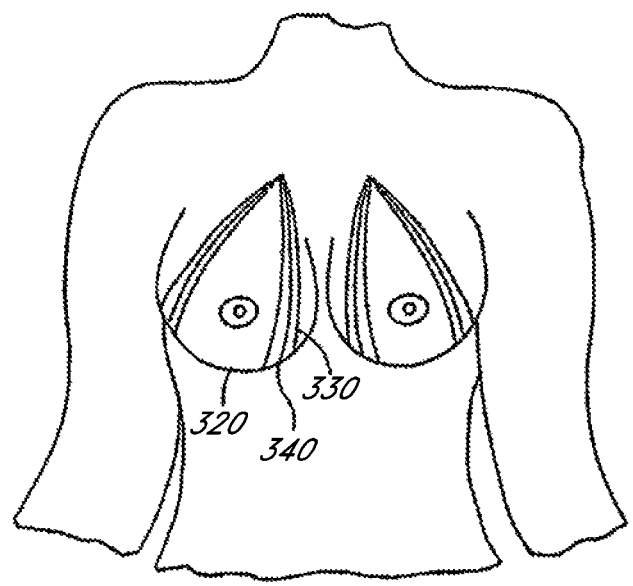
FIG. 20 is a front view illustrating a placement of sutures to perform a breast lift procedure.

In some embodiments, sutures of the present disclosure are used to perform a minimally invasive breast lift, as shown in FIG. 19. In one method, suspension members 330 are inserted through the skin and advanced at a depth of between about 2.5 and 25 mm under the skin surface. The suture is passed through the Cooper's ligaments and fatty tissue. One or more loops of suture material are looped under the breast 320, and suture ends are attached to an area in the chest 342, serving as anchor points for the suspension members 330. The sutures are tensioned in order to simulate support provided by natural, healthy Cooper's ligaments, as shown in FIGS. 19 and 20, and are effective to lift the breast 320 (compare left and right panels in FIG. 19).

In some embodiments, the attachment to the chest areas comprises a loop of suture material threaded around a portion of the pectoral muscle, fascia, sternum, a rib, or a ligament, or combinations thereof. The loop is inserted through the skin with a small caliber needle, and positioned below the top edge of the breast, so that the suture support is not visible through the skin. A curved needle attached to the suture can be used to insert the suture material. In some embodiments, the needle comprises two parts that are axially movable relative to each other, and which have different curvatures, such that the surgeon can adjust the curvature of the needle is it is being inserted. In some embodiments, the suture is delivered within a sheath.

In some embodiments, the anchor can comprise a bone screw, attached to bone or cartilage in the sternum or rib cage.

In some embodiments, a suture 330 can run from the anchor point 342, along one side of the breast 320, under the breast, and up the other side back to the anchor point 342. A number of sutures 330 placed in this way will be effective to cradle and lift the breast from below. In some embodiments the sutures 330 could run down either side of the breast and attach at support points 340 either under or to one side of the breast. A number of possible ways of placing and orienting sutures will be possible in achieving lifting of the breast while maintaining breast symmetry and aesthetic appearance. These various arrangements and combinations will be apparent to those of skill in the art.

In some embodiments, the suture lines can be extended transcutaneously around the nipple area to preferentially reposition this portion of the breast. This corrects the situation where the nipple turns downwards in response to age or as a result of breastfeeding. Looping a suture line around the nipple provides for support of the nipple, without having to support the entire weight of the breast. Where a nipple repositioning technique is used, the suture can be anchored using the methods as described above.

In some embodiments, lifting of the pectoral muscle is used to adjust the physical appearance of the breast. A method to modify the muscle tissue by shortening it can comprise cutting the muscle and drawing it together, or drawing it together using a series of threads similar to a corset. Lacing the tissue together results in lifting of the breast tissue resulting in a more youthful appearance, and a reduction in breast ptosis.

In some embodiments, shortening of the muscle fibers is accomplished by internal anchors deployed into the muscle fibers. Drawing the anchors together in turn draws the muscle tissue together. The anchors can be connected by suspension members comprising elastic or inelastic materials. Elastic material can be used to allow for normal loading conditions such as physical movement and activity. Additionally, elastic materials can result in further lifting of the breast tissue.

Elastic material examples can include, without limitation, silicone core braided materials similar to a "shock cord" construction, polypropylene mesh as used in hernia mesh, NiTi alloy wires or braids, coiled type springs, and similar materials and combinations known in the art. In some embodiments the materials distribute the entire load throughout the length of the suspension line limiting longitudinal movement. In some embodiments, the suture lines comprise relatively inelastic materials including, without limitation, polypropylene suture, NiTi wire, stainless steel wire, polypropylene mesh and the like. These materials can be attached to anchors such as barbs, hooks, flared materials such as NiTi elements and the like.

This system can be foreshortened during initial implantation or post implantation with mechanisms such as, and without limitation, screws, loops, cams and rotary pulleys, or any other means effective to shorten thread or wire-like elements. The muscle can be additionally suspended by hernia mesh material and tied to land marks such as, without limitation, bone, fascia, tendon, and other areas that would bear the loading conditions. In some embodiments an exemplary diameter of a suspension line can range from about 0.005 inches to about 0.090 inches. In some embodiments the diameter of a suspension line would be about 0.030 inches.

In some embodiments the material permits tissue ingrowth, and thus moves with the native tissue, reducing irritation and cutting of the tissue. The material can be coated with a therapeutic agent to enhance tissue ingrowth, and in some embodiments the suture material is manufactured to include the therapeutic agent. In some embodiments, the therapeutic agent is added just prior to implantation, either by impregnation, by coating, or by a combination of the two processes.

In some embodiments, coatings or treatments can include a inhibitory agent to limit or prevent tissue ingrowth such that the material will not adhere to the surrounding tissue. In some embodiments a suspension line runs through a cylinder of fluid that allows movement between the suspension line and the tissue.

Figure 21:
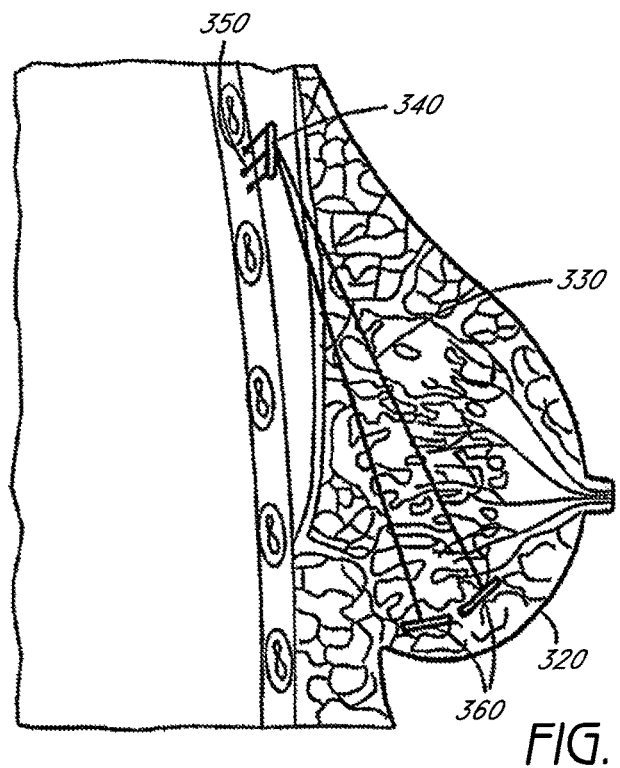
FIG. 21 is a side view of a breast and an embodiment of a support system comprising a support member and vertically oriented suspension members.
Figure 22:
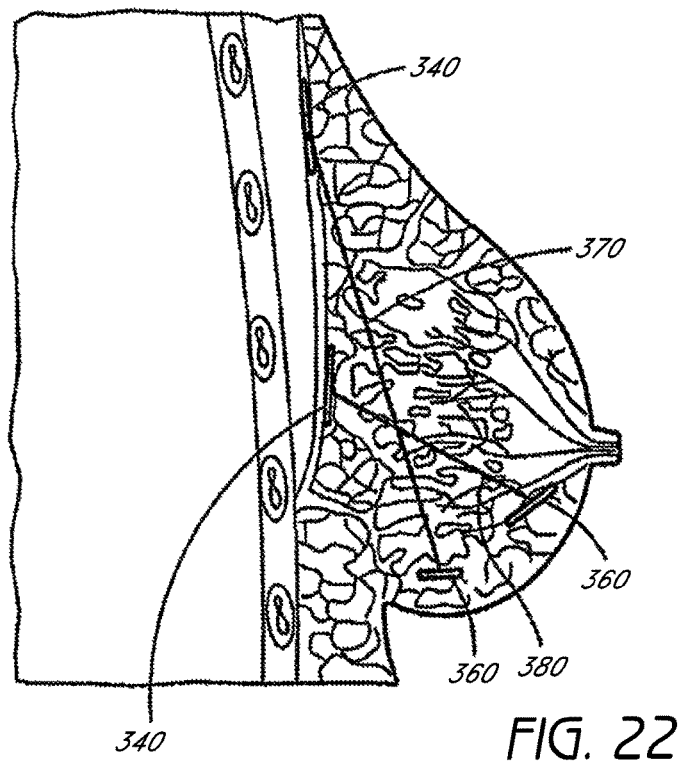
FIG. 22 is a side view of a breast and an embodiment of a support system comprising a support member and suspension members oriented vertically and non-vertically.

In some embodiments the support system comprises suspension members 330 are provided that are oriented in a substantially vertical orientation, as shown in FIG. 21, and attach to an anchor point 340 above the breast. The support members 360 are coupled to the suture lines 330. In some embodiments, angles for suspension members other than vertical are used to customize the shape of the breast or where the procedure is used to correct breast asymmetries. As shown in FIG. 22, angled suture lines 380 can provide lifting or additional lateral adjustment, in addition to what can be provided using vertically oriented suspension members. For example, by placing the support lines angled either to the right or left of vertical, the nipple and/or breast may be adjusted medially or laterally as desired by the surgeon, in addition to vertical repositioning. In some embodiments, a vertical support line and secondary tensioning line can be used, and the vertical lines can thus be pulled laterally, redirecting the force vector supporting the breast tissue. In some embodiments, it can be useful to provide laterally oriented suspension members alone, such as where lateral repositioning is required, but lifting is not desired or otherwise indicated.

Figure 23:
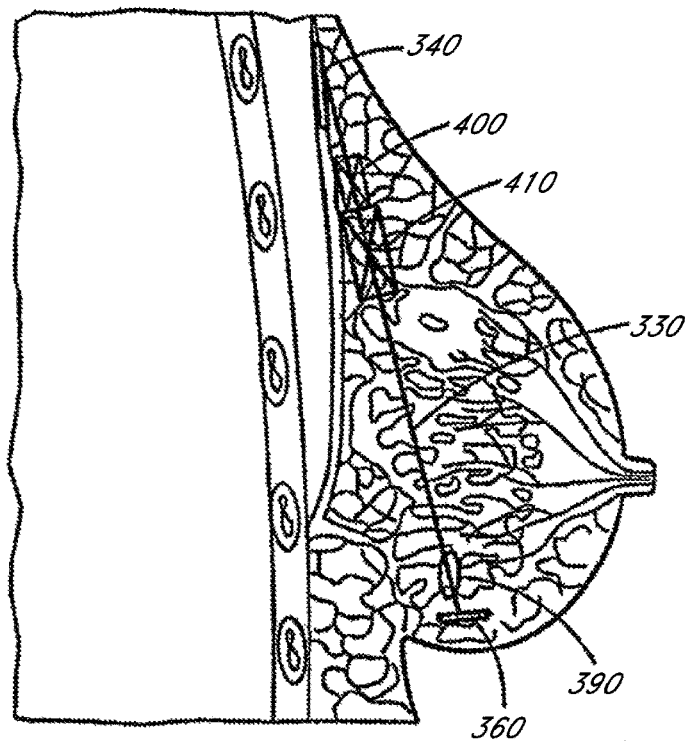
FIG. 23 is a side view of a breast and an embodiment of a support system comprising two types of elastomeric components, and a safety mechanism to prevent overloading of the tissue.

In some embodiments, the support system comprises components with nonlinear elastic constants (e.g., a secondary elastomer to increase the load bearing at the bottom of the stroke). This allows for normal support while standing, and provides additional load bearing capacity during activities such as walking. running, and jumping. In some embodiments, components that allow for complex loading are designed using larger cross sectional areas or by providing components fashioned from more than one material, where the individual materials have distinct elongation characteristics. In some embodiments first 400 and/or second 410 elastic components can be used to provide more complex mechanical behavior, as shown in FIG. 23. In some embodiments, the first and/or second elastic components can comprise springs. In some embodiments, the first and second elastic components can have the same or different elastic constants. In some embodiments, the first and/or second elastic components can be positioned anywhere along the length of a suspension member.

Safety Disconnect

In some embodiments, a safety release 390, shown in FIG. 23, provides a mechanism to protect the attachment area or the supported tissue from damage caused by support system components when large loads are imposed on the tissue and/or the support system. For example, excessive load can occur during excessive motion or concurrent with a trauma. The safety release 390 is designed to separate the support member 360 from the suspension members upon exceeding a defined loading.

In some embodiments, the safety release 390 comprises a region engineered to fail at a predetermined limit. In some embodiments the mechanism comprises a necked section to allow for yielding. In some embodiments, a slip disconnection that decouples, or a joint that unlatches can be examples of effective safety releases. In some cases the safety release mechanism can be designed such that it can be reconnected or repaired following release. The loading limit effective to result in release of the suspension members from the support member can range, for example, from about 0.5 kg to about 8 kg, and in particular from about 1 kg to about 3 kg of force.

Figure 24:
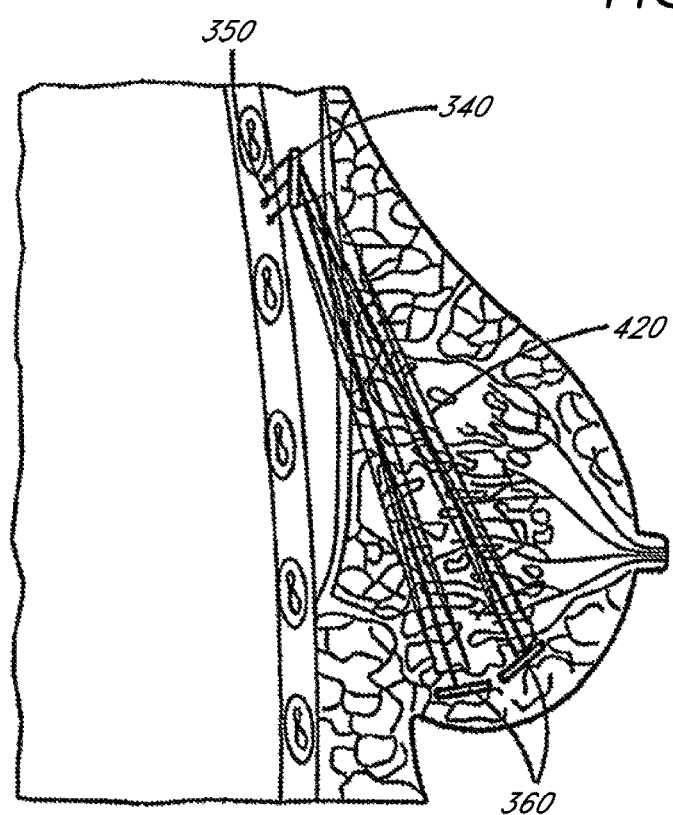
FIG. 24 is a side view of a breast and an embodiment of a support system comprising continuous length suspension members, and a length adjustment mechanism.

In some embodiments, selecting the elastic characteristics of the support member to carry partial or complete loading can allow for a least amount of tissue movement relative to the suspension element. In some embodiments, the entire length of the support system can assume the stress where the least amount of movement is shared throughout the entire system. Continuous length elastic elements 420 can be used to support the loading to lessen the stress concentrations in one area of the implant, as shown in FIG. 24. In some embodiments, the system can also include an adjustment mechanism 350, useful to vary the tension exerted on the tissue by the support system either at the time of implantation, or later once the healing process is complete or near complete. Adjustments could also be made over extended times in order to maintain the supported tissue in a desired position.

Support Member with Inflation Pleats

In some embodiments, the support member can include additional load carrying or shock absorption capability. For example, hydraulic (gas or liquid) elements can provide a resilient cushion in order to compensate for various loading conditions, such as jogging and other sporting activities, or to absorb some of the effects of trauma. In some embodiments, shock absorption is provided by a support member comprising inflation chambers 430. The chambers can be configured to compress during heavy loading, with compression providing the resiliency to return the device to a pre-loading configuration once the activity or other source of loading has ended. Similarly, the system can include a charged system, analogous to an automotive shock absorber, to dampen loading, and where the charge would allow for recoil loading.

The chambers can have a wall thickness in a range, for example, from about 5 µm to about 250 µm, depending upon the material, the inflation pressure to be used, and the degree of resiliency desired. There can be a single chamber or multiple chambers. Material choice, chamber wall thickness, and/or inflation pressure can provide customized mechanical properties to support members. In some embodiments, the length of the chambers ranges from about 5 cm to about 15 cm, and width ranges from 0.5 cm to about 4.0 cm. In some embodiments, the length of the inflation chamber is about 10 cm, and the width is about 3 cm. Precise shapes and dimension can be varied depending on the particular anatomical makeup of the patient, or on the kind of support or aesthetic results desired.

In some embodiments, the chamber(s) can be filled with a media that solidifies or gels. In some cases, the media remains in a liquid form. Composition of the media can include, without limitation, silicone, saline, epoxy, and any other safe implantable fluids, solids, or gases that will be substantially retained within the chamber(s).

Figure 25:
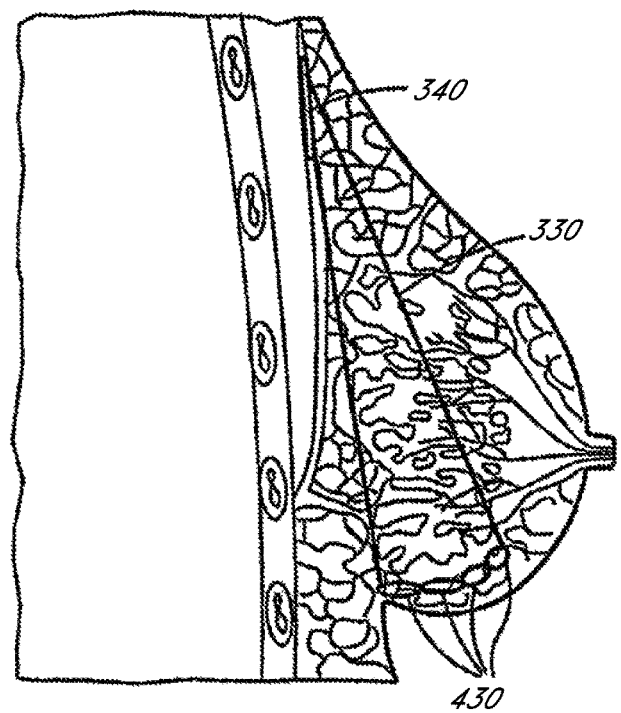
FIG. 25 is a side view of a breast and an embodiment of a support system where the support member comprises inflation chambers.

In some embodiments, addition of one or more volume elements supported by suspension elements can be used to augment low volume breast tissue and enhance the final outcome with respect to a patient's fullness. The volume element can comprise a prior art augmentation device such as a silicone or saline implant or it can use a dermal filler to soften the look of the breast. In some embodiments, support members comprising chambers 430, an example of which is illustrated in FIG. 25, can be adapted to provide volume enhancement. Fillers can include, without limitation, commercially available materials such as Radiance, Juvederm™ or other suitable filler materials. Additionally, the patient own cells or other tissue could be used to offset the decrease or need for additional filling. These cells could be harvested and replaced or harvested and processed by centrifuging or filtering to collect cells suitable for implantation.

In some embodiments, different connection points for suspension and support members can be used to adjust the position of each breast separately, or to allow shape changes that improve the cosmetic appearance of the breasts, for example to provide symmetry.

Folded Support Member for Easier Insertion

As described above, in some embodiments the support system is folded prior to delivery. Folding reduces the device profile, such that a smaller incisions can be used to provide an entry point when introducing a support suture or system into the body. The smaller incision in turn limits the size of the scar resulting from the implant procedure. A number of manipulations well known in the art including, without limitation, rolling, folding and twisting of the support member, can be used to reduce the device profile prior to delivery.

Figure 26:
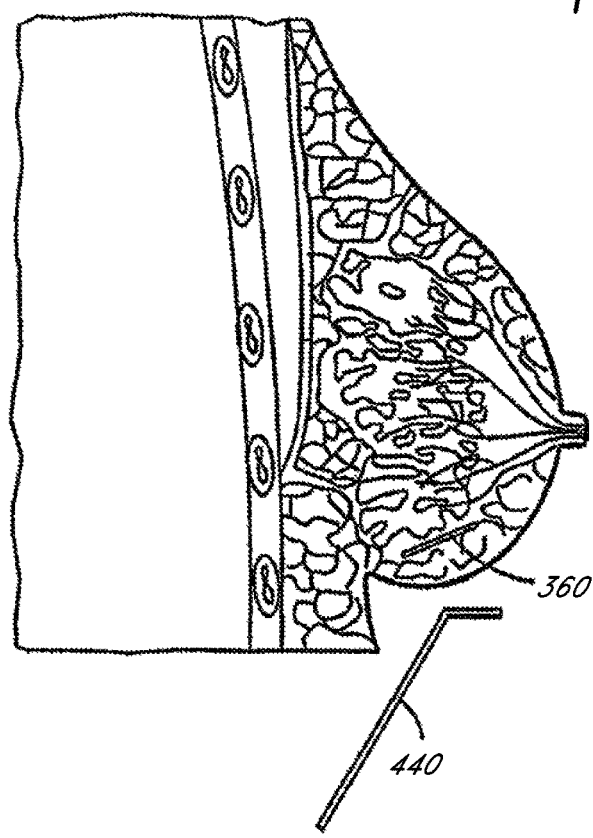
FIG. 26 is a side view of a breast and an embodiment of a tool for inserting and spreading or flattening a support member in the tissue.

Post insertion the mesh support member can opened and flattened for final placement. In some embodiments, the unfolding process is performed using specialized instruments, such as a small tool 440 in similar in shape to a "hockey stick" as shown in FIG. 26. Spoon shaped tools are also effectively used to unfold and place the device in the desired location.

Support System Including Barbed Elements

Figure 27:
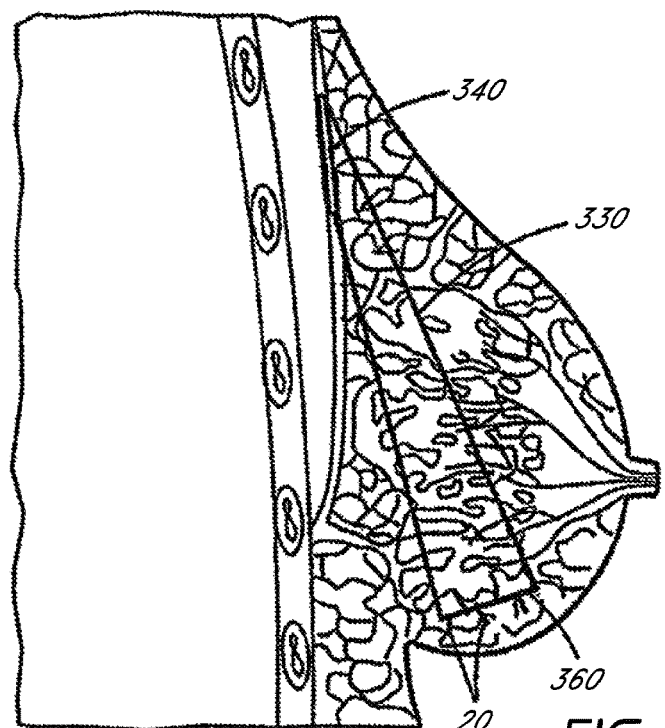
FIG. 27 is a side view of a breast and an embodiment of a support member comprising barbs.

In some embodiments, the support member 360, the suspension members, or both, can comprise engagement members, for example, barbs 20, as shown in FIG. 27. Barbs are effective to improve engagement of the adjacent tissue and reduce movement of the support system relative to the tissue. Barbs can be fashioned from materials similar to those used to construct the support member or suspension members, including, without limitation, stainless steel, Nitinol and any other biocompatible materials.

In some embodiments, the barbs can be from about 0.25 mm to about 2 mm in diameter, and from about 0.25 mm to about 5 mm in length. In some embodiments the barbs are 0.5 mm in diameter, and about 2.5 mm in length. These are examples of barb dimensions and other dimension of barbs can be used without limitation. Barbs can be oriented all in the same direction or they can be oriented in alternate directions in order to provide resistance to both proximal and distal movement.

Other Suspension Elements

Figure 28:
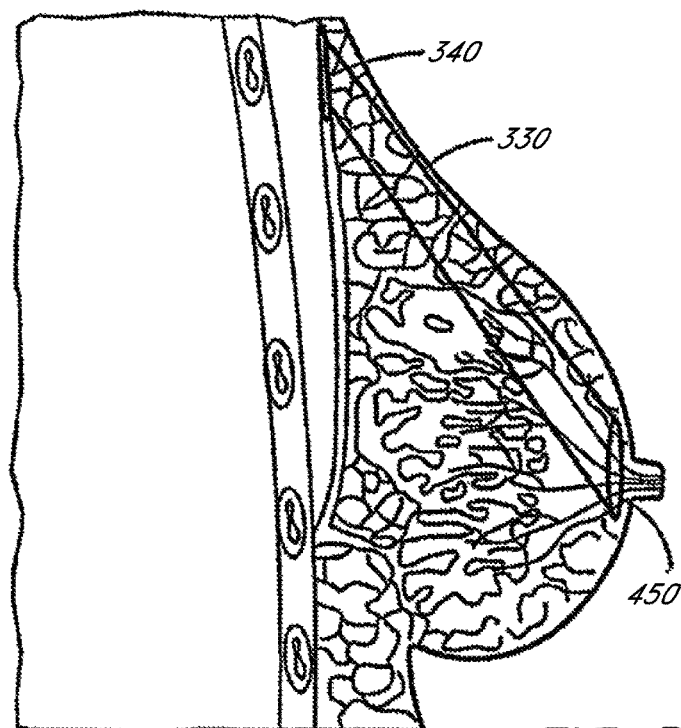
FIG. 28 is a side view of a breast and an embodiment of a support system comprising a nipple repositioning element.

In some embodiments, the device can comprise a nipple suspension element 450 to raise the nipple and/or reposition it with respect to the support members, as shown in FIG. 28. Positioning the nipple using a separate element allows for separate positioning of the breast relative to the nipple. including addition suspension or tensioning elements provides the ability to make vertical and/or horizontal adjustments to the nipple.

Additional Support System Components

Figure 29A:
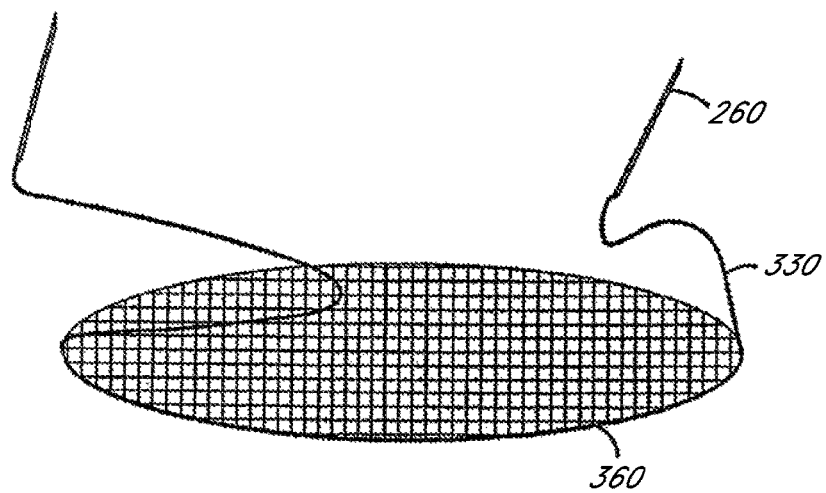
FIG. 29A is an embodiment of a support member, associated suspension members, and needles for insertion.

In some embodiments, the support system can comprise a webbed, or mesh, support member 360, suspension members 330, and attached needles 260 for insertion into the patient, as shown in FIG. 29A and B. In some embodiments, the suspension members and support members can comprise a contiguous structure. In some embodiments, the suspension members and support member can comprise separate pieces that are assembled prior to use.

Figure 29B:
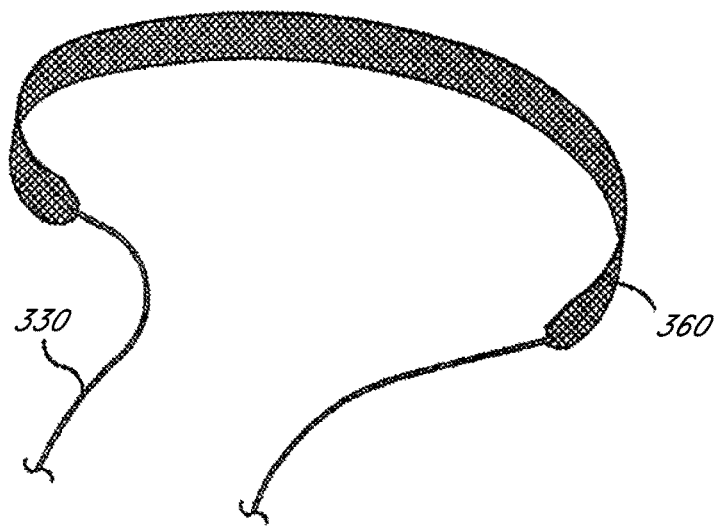
FIG. 29B is a photograph of an embodiment of a support member and attached suspension member.

Conveniently, in some embodiments, the support member can be fashioned in the shape of a sling or hammock, an example of which is shown in FIG. 29B. As used herein, the term "sling" or "hammock" is intended to include, without limitation, a wide variety of shapes and sizes, materials and treatments. A sling (or hammock) can be rectangular, other shapes are also contemplated included oval, circular, elliptical, and tear drop shaped. In some embodiments, the sling can be made of a mesh material. The mesh material can comprise one or more woven or inter-linked filaments or fibers that form multiple fiber junctions throughout the mesh. The fiber junctions can be formed via weaving, bonding, ultrasonic welding or other junction forming techniques, and combinations thereof.

Figure 30:
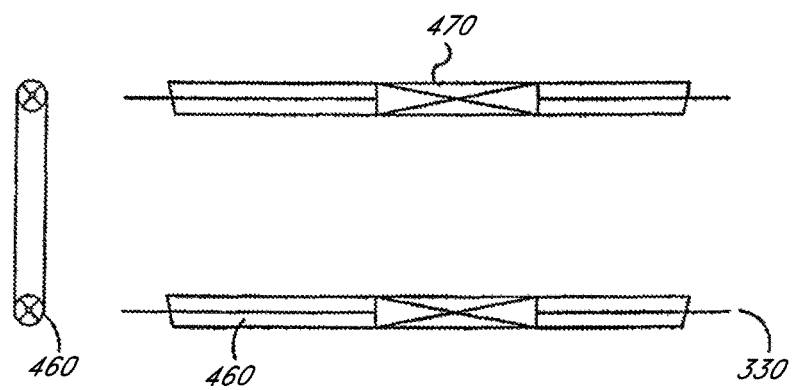
FIG. 30 illustrates an embodiment of a support system including channels for the suspension members, and spring elements.
Figure 31:
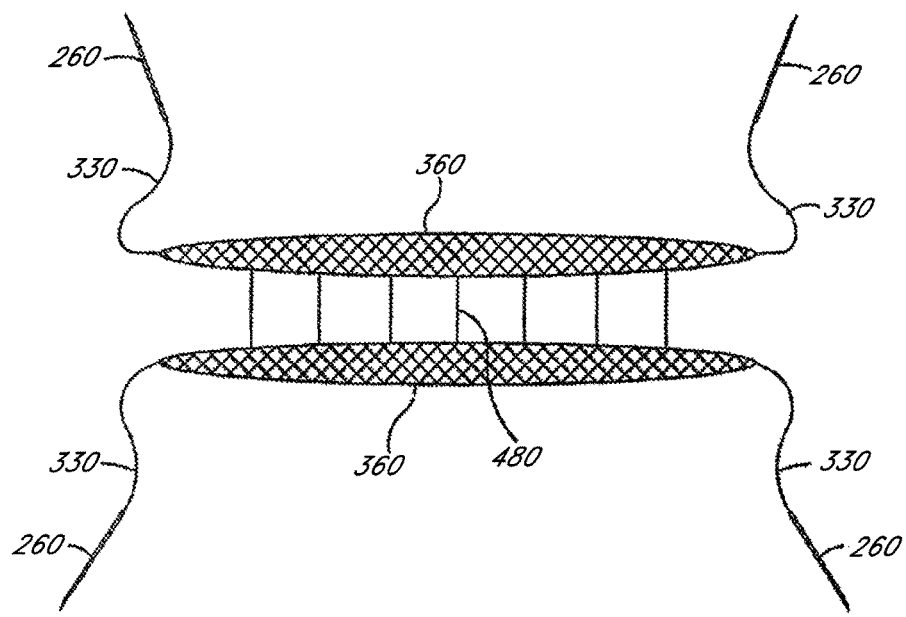
FIG. 31 illustrates an embodiment of a support system comprising separators to maintain spacing between adjacent support members.

In addition to suspension members and a support member, a support system can comprise additional components. For example, channels 460 can be used to hide the wire or springs 470, which can be effective to eliminate irritation to the surrounding tissue, as shown in FIG. 30. These channels may be open or closed to either allow or limit contact with body fluids. In some embodiments, the channel may utilize a perforated channel to allow fluid to flow or move within or around a wire or spring. In some embodiments, fluids in channels can serve as a lubricant for suspension members within channels.

Where multiple support members are used, separation of the elements can be provided, as shown in FIG. 31, by separators 480. One or more separators 480 between support members 360 can be effective to limit motion of support members relative to each other. Separators can resist movement of elements toward or away from each other by geometric column strength or tensile stress, respectively. In some embodiments, separators 480 can be measure about 0.25 mm to about 2.5 mm in diameter with a length of 0.5 mm to about 8 mm. It will be understood that these dimensions are exemplary only, and other dimensions of separators can be successfully used. A variety of materials can be used to make separators, including without limitation, plastics, polymers, metals, and these materials can be permanent or absorbable.

Maintaining a defined separation of support members during or post implantation provides for more even suspension of tissue with loading distributed across the effective area encompassed by the support member(s). Embodiments of support members can be provided as a mesh material with different patterns depending on the loading or stress expected. Additionally, support members can be fashioned with a preset shape effective to resist collapse when the ends are tensioned as during loading.

A wire mesh work made from NiTi or stainless steel can allow for a flatter looking implant during loading, whereas a limp thread element may provide little support on the sides of the breast when loaded. This allows for a rounder shape definition rather than squeezing at each side of the breast during loading. The wire elements can be pre-shaped and memory set to allow for normal motion and tissue manipulation.

Figure 32A:
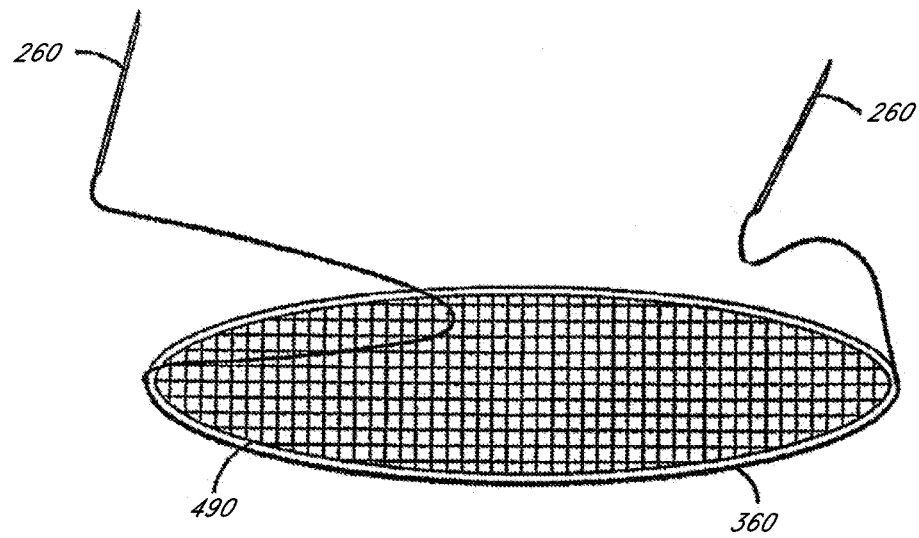
FIGS. 32A-B illustrates an embodiment of a support system including an additional structural support member.
Figure 32B:

For example, as shown in FIG. 32A, a wire support 490 included in the support member 360 mesh can increase strength and provide means for coupling the support member to other components of the system. By adding additional components to the support member, properties of strength or elasticity can be imparted, depending on the choice of materials, for example, and without being limiting, elastomers, pre-shaped shape memory elements, springs and the like. These additional elements can be located above or below the mesh or embedded into the mesh for motion encapsulation. FIG. 32B illustrates an embodiment of a wire support 490, separated from the support member 360.

Insertion Method

Figure 33A:
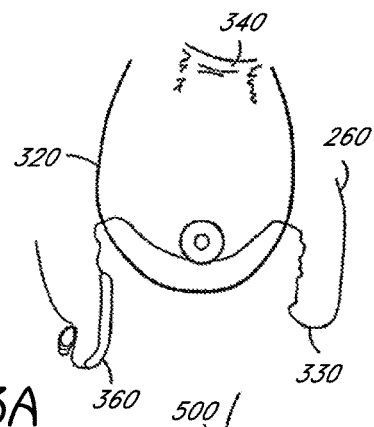
FIG. 33A-F illustrates a method of surgical placement of an embodiment in a breast lift procedure.
Figure 33D:
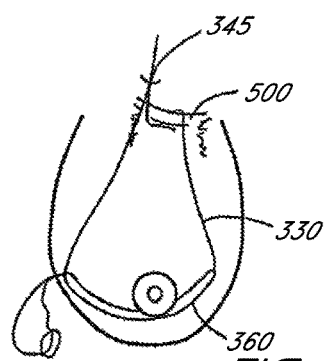
Figure 33B:
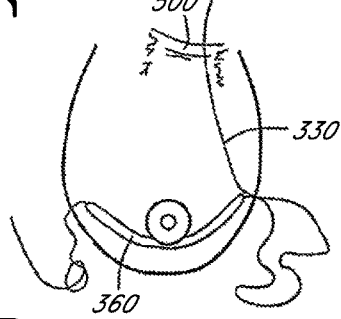
Figure 33E:
Figure 33C:
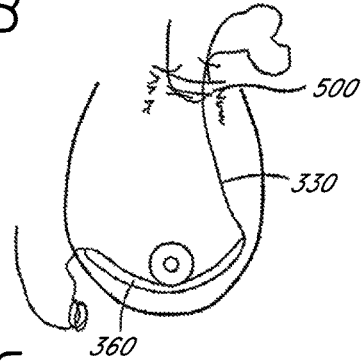
Figure 33F:
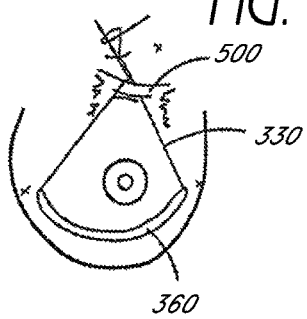

In some embodiments, there is also provided a method of insertion of the device, as shown in FIG. 33A-F. In one embodiment, insertion is performed by a needle 260 inserted at the base of the breast 320, exiting the other side of the base, and pulling the support member 360 through the tissue between the glandular structure and the subcutaneous fat (FIG. 33A). Once the support member 360 is positioned correctly, the needle 260 can be passed back into the same needle hole and vertically to the anchoring position (FIG. 33B). As the needle is passed back into the fascia of the pectoral muscle, the piercing of the fascia is captured and the needle is once again pulled out of the transcutaneous needle hole (FIG. 33C). In the same fashion the other support line can be passed and the fascia again can be captured and tied to the other support member where a knot pusher can be used to slide the knot 345 deep beneath the skin where it can be hidden to avoid producing a bump that might otherwise show on the surface of the skin (FIG. 33D). Anchoring of the support system can be achieved by looping or otherwise tying the ends of the suspension members to a suitable anatomical feature, such as a bone 500, for example (FIG. 33E & F).

Some embodiments of a method of insertion of support system include an initial pathway being introduced under the skin with a guidewire system, and providing a tubular sheath for guidance, along with the ability to exchange wires. A tubular sheath allows the surgeon to maintain access to a common pathway for device installation and manipulation. The guidewire can be introduced under the skin through a small trocar or needle where the softer tubular sheath is exchanged out, and other elements can be passed through such as thread, suspension elements, and the like. A larger incision at the lower portion of the breast can be used to introduce a wider support member, for example a sling or hammock as has been described herein. This can include an incision to introduce the wide sling at one or both sides of the breast. Additionally, these techniques could be all completed in an open procedure as normally seen in a mastopexy operation.

Additional Exemplary Procedures

Embodiments of sutures as presently disclosed can be used to resuspend loose tissue in the neck region. A suture can be inserted using a similar technique as that used for a breast lift. The suture can also be configured to spread out support over multiple lines, or using slings or other types of configurations as described above, so as to prevent the cheese wiring effect that can occur when using a single thin-lined sutures. Designs applicable for use in breast lift procedures, are thus equally applicable for use in a neck lift procedure.

As shown in FIGS. 34A-B, in one method, the suture 510 is inserted under the skin surface and advanced below the surface following a line extending along the crease in the skin where the underside of the jaw area meets the neck. In some embodiments of a neck lift method, the upper portion of the suture 510 is turned upward and extended posteriorly to the jaw bone, as illustrated in both FIGS. 34A and 34B. The suture can be anchored 340 with a loop of suture material to the connective tissue located behind the jaw bone and just below the ear, as illustrated in FIG. 34B.

Embodiments of barbed sutures can be used effectively to lift tissue in the lower thigh area that has sagged down above the knee, as can occur during aging. Sutures with barbs at either end can be inserted from above the skirt line and used to pull the skin from the lower thigh up towards the tissue in the upper thigh area. The barbs located in the part of the suture located in the upper thigh region can be anchored to the dermis, or to tendons, ligaments, bone, or muscle, further below the surface. The portion of the suture located in the lower thigh area can engage the dermis or fascia, or other tissue, typically at a depth of 0.2 to 20 mm below the skin surface. A method similar to that used to lift thigh tissue can be used in the region of the upper arm.

Embodiments comprising barbed sutures can also be used to engage muscle. For example, in some embodiments, sutures can be placed in the abdominal region, and then tensioned to pull the abdominal muscles back into position. In some embodiments, the method can further providing a support system comprising a series of tabs 530 and sutures 540. In these embodiments, additional tension can be applied to the sutures, while at the same time avoiding pulling the suture through or otherwise tearing the tissue to which they are attached, or through which they have been threaded. By weaving a series of line from one tab to the other, the muscles can be further supported, for example as illustrated in FIG. 35. The tabs can be inserted by a small incision, and placed under the skin. Suture material can be pre-loaded into each tab, and sutures connected to each other by a transcutaneous knot or series of knots.

As shown in FIGS. 36A-B, embodiments comprising barbed sutures can also be used to improve upon prior art methods of performing facelift procedures. In the prior art methods, shown in FIG. 36A, sutures 550 are inserted under the skin near the front of the cheek, pass up towards the hairline, where they exit out of the skin. This method leaves exposed suture ends 560 near the front of the face, which are unsightly. Although these ends can be trimmed such that the ends lie under the surface of the skin, as shown in FIG. 36B, over time it is possible for these ends to erode through the skin and reappear.

In contrast, in some embodiments of the present disclosure, the suture 550 is fashioned to have barbs at a first end of the suture. The barbs are effective to engage the tissue and resist movement (or to create tension) once in place. The first end can be delivered into the facial area through a trocar. In some methods, the insertion point of the trocar can be above the hairline. Once the first end is in the desired position the trocar can be removed wherein the barbs are exposed to, and ultimately engage, the surrounding tissue. Tension can be applied to better secure the barbed end of the suture within the tissue. The suture can optionally include markings that inform the surgeon how deeply the suture has been placed. If placement is unsatisfactory, the same trocar, or a second trocar, can be inserted over the suture to facilitate removal and/or relocation. The method obviates the need for an insertion point near the front of the face, and further avoids having suture ends exposed in the facial region, as occurs with the prior art method.

Once the first end is in place, the second end of the suture can be anchored in the scalp, or other suitable region. The second end can also include barbs to improve anchoring. To place the second end, the end can connected to a long needle. The needle can be inserted through the same hole where the trocar was inserted and then advanced up the scalp. In some embodiments, the distance is from about 3 inches to about 7 inches, although this is not limiting. The suture can be exited through the skin, and satisfactory tension on the suture can be achieved by pulling on the exposed end. In some embodiments, the free end near the hairline can be trimmed to below the surface of the skin. In some embodiments it can be useful to re-tension the sutures after the barbed portions have healed into the tissue. In these cases, a short portion of the second end of the suture can be left protruding from the scalp to enable the surgeon to access it more easily at a later date. The end can be covered with a small adhesive bandage, or with a liquid bandage in order to protect the end.

Use of the above described techniques can be useful if providing lifting for this buttocks region. In the buttocks, single or multiple support systems can be used. The system can designed to provide for additional load bearing, while preventing cutting or tearing of supported tissue during movement associated with normal activity. One end of the support system can be attached to the outer hip, while the opposite end can be attached to the upper hip bone. Anchoring in this way provides that the support can function effectively under either static or dynamic loading conditions. In some embodiments, the use of crescent shaped support straps can be used to accommodate the majority of the tissue to be supported. Additional branch suspension members can be included to allow for further lifting and shaping of the tissue. Barbed sutures can be used to improve anchoring within tissues.

Materials & Construction

Elements of the support system can comprise a number of materials including, without limitation, biocompatible polymers (e.g. ePTFE), intestinal sub-muscosal mesh, tendon, Gore-Tex®, and polypropylene. Materials can be monofilament, or multifilament, and can be braided, woven, or knitted. In some embodiments materials are absorbable (i.e., biodegradable). In some embodiments, the materials comprise coatings or other agents that promote healing, reduce inflammation, or improve biocompatibility.

In some embodiments, the use of biological materials can improve tissue interaction with the device. Where a lack of tissue ingrowth or vascularization is a concern, the materials can be further modified by perforation, or by other treatments such as fixation with radiation, glutaraldehyde, heat or 1-ethyl-3-(3-dimethylaminopropyl)-carbodiimide (EDC), to improve porosity.

In some embodiments, the mesh material of the support member, for example a sling or hammock, comprises a flexible, polypropylene monofilament that resists weakening or degradation when implanted within a patient. One such material is Marlex™. Other mesh and non-mesh materials, can comprise, but are not limited to, synthetic biomaterials, allografts, homo grafts, heterografts, autologous tissues, materials disclosed in U.S. provisional application Nos. 60/263,472; 60/281,350; and 60/295,068; the contents of all of which are herein incorporated by reference in their entireties, synthetic materials (such as metallics, polymerics, and plastics) and any combinations thereof.

In some embodiments, the support member material will result in minimal or no reaction with body tissues and fluids and indefinitely retain its particular material characteristics and mechanical properties. Further, portions or all of the support member can be configured or fabricated from a material to either promote or prevent tissue in-growth, or are resorbable.

In some embodiments, the support member, support member assembly or portions thereof, can have one or more substances associated therewith through processes such as coating, impregnation, or combinations of these processes. Examples of appropriate substances include, without limitation, drugs, hormones, antibiotics, antimicrobial substances, dyes, silicone elastomers, polyurethanes, radiopaque markers, filaments or substances, anti-bacterial substances, chemicals or agents, and any combinations thereof.

The substances can be used to enhance treatment effects, reduce potential rejection by the body, enhance visualization, indicate proper orientation, resist infection or other effects. For example, a dye may be coated on one surface of a component of the support system. The dye can provide the practitioner/surgeon with a visual indicator to aid in orienting the support member or suspension members at the target site within the patient and to avoid undesirable twists along the length of the system. As another example, the system may be coated by the process described in U.S. Pat. Nos. 5,624,704; 5,756,145; 5,853,745; 5,902,283 and 6,162,487; the entire contents of which being hereby incorporated by reference.

It will be apparent to those skilled in the art that varying geometries for the components of the device will be useful. For example, certain dimensions of thickness, width, or length will be recognized as being of particular advantage. In addition, components that are woven, braided, wide or narrow can also provide particular support functions.

For example, as described above, in some embodiments the support member comprises a "hammock" or "sling" shaped element. A sling or hammock can be especially useful for supporting glandular tissues, such as breast tissue. In some embodiments, a hammock with dimensions of about 7 cm to about 15 cm in length, and about 2 cm to about 5 cm in width, with a pocket of about 0.5 to about 3 cm, provides effective tissue support. In some embodiments, a hammock can have a length of about 10 cm, a width of 2.5 cm and a pocket depth of about 1 cm. In manufacturing a hammock, the particular shape can be formed by wrapping the material about a spherical or elliptical shaped mandrel, followed by heating and cooling the mandrel to induce the material to conform to the shape of the mandrel.

A sling (or hammock) can comprise first and second major surfaces, a pair of end portions, and a support portion for placement in a therapeutically effective position relative to a physiological environment intended to be supported (e.g. the glandular tissue of the breast). In some embodiments, the sling has a tension adjustment or control member associated with the sling, for transferring sling adjustment forces from one portion of the sling to other portions of the sling such as the ends of a support portion of the sling. The member affords effective repositioning of the sling while avoiding undesirable permanent deformation of the sling.

The support member can be substantially surrounded by a protective sheath. The support member, tension control element, and sheath can be made of biocompatible materials with sufficient strength and structural integrity to withstand the various forces exerted upon these components during an implant procedure, and/or following implantation within a patient. In some embodiments, the protective sheath is constructed of a material that affords visual examination of the implantable support member material and that affords convenient passage of the assembly through tissue of the patient.

In some embodiments, a woven mesh with a predetermined pore or opening size to permit tissue ingrowth can be used. These shape of the openings is not considered limiting to the scope of the present disclosure, and square, rectangular, and/or round openings are useful. In some embodiments the size of the openings can vary, for example and without limitation, from an area of about 0.1 mm$^2$ to about 30 mm$^2$. The arrangement of pores can vary throughout the device in order to provide some areas with added porosity, or to provide more support. Some areas can comprise pores, while in other areas pores can be absent. The device can be produced from elastic materials, or alternatively can be fashioned from relatively rigid materials.

In some embodiments, the mesh-like support member is woven from a monofilament line. Some monofilament lines are finished with a smooth surface, while others are roughened during the manufacturing process. Roughening the surface increases surface area and thus increases opportunities for tissue ingrowth throughout the surface interstices.

Roughening can be accomplished during the extrusion process where the material is flowing through the extrusion die hot thus creating a dimpled surface. Other roughening methods include, without limitation, sanding, grinding, roll forming, laser etching, chemically etching, and spirally or radially scoring to a predefined depth with a cutting blade, laser, or other means. Examples of sanding may use a 5-100 µm grit sand paper pulled across the material. This drags portions of the material along the longitudinal axis and leaves behind whiskers or microscopic barbs that can also be effective to engage the tissue. A similar process could be used with a grinding wheel. Grinding can be performed in a radial pattern, a helical pattern, or a combination of patterns. Roll forming allows for a predetermined shape or pattern to be pressed into the monofilament, and can be performed either with a heated roll or at ambient temperatures.

Laser etching allows for an inline process to be added to the formation of the monofilament. The laser can be angled or focused directly perpendicular to the material. Chemical etching removes material at a predictable random pattern and a predefined depth based on chemical strength and length of contact with the material being etched. Other materials can be plasma etched to create a desired surface finish where a chamber is pumped to a preset base pressure and gas is introduced and a radio frequency field is applied to the electrodes of the chamber producing a glow-discharge plasma.

Knife scoring allows a partial cut to the material to a predetermined depth leaving behind a ribbed monofilament material that will be more flexible and allow tissue ingrowth to the cut sections. These cuts can also be in a spiral patterning to allow a continuous cut throughout the material length. This also allows for tissue ingrowth.

In some embodiments, partially or completely absorbable materials are used, such that a component(s) can be absorbed over a period ranging from about 6 weeks to about 2 years. This allows the skin and other tissues to retighten and remodel, while otherwise being supported in a desired position. Other methods are also useful in remodeling or tightening the skin around the breast including, without limitation, forced scarring, use of laser, heat, and the like.

In some embodiments, the overall dimensions of the support member assembly, including individual sheath, mesh element and tension control member, are effective to extend from the upper most connection point down partially encircling the lower portion of the breast and back up to the upper most portion of the connection point, with additional length to account for the imprecision associated with the range of human anatomy sizes. In some embodiments, the support member has a length X, width Y and thickness approximately within the range of 8 cm to 16 cm, 1.0 cm to 6.0 cm and 0.10 mm to 1.0 mm, respectively. In addition, the length of the tension control element can be approximately equivalent to or slightly longer than the length of the support member to tighten or loosen the sling after it is placed in the body. Alternative lengths, widths and thicknesses can also be used, depending on the particular anatomical features of the individual patient, and the tissue(s) being supported.

In addition, the size of the resultant openings or pores, in support members configured as a mesh, can be adapted to allow tissue in-growth and fixation within surrounding tissue. The quantity and type of fiber junctions, fiber weave, pattern, and material type influence various sling properties or characteristics. Non-mesh sling configurations are also included within the scope of the invention.

As an example, and not intended to be limiting, the mesh can be woven polypropylene monofilament, knitted with a warp tricot. The stitch count can be 10±1 courses per cm, and 5±1 wales per cm. In an exemplary mesh, the mesh thickness can be 0.6 mm.

The support system of the present disclosure is not limited by the need for additional sutures or other anchoring devices, although such sutures and devices can be used if desired. The frictional forces created between the system and patient tissue are effective to prevent movement and loss of tension once the system is properly located at the target site. As a result, the system remains securely in place, even when subjected to various forces imparted on the tissue as will in the patient during various activities.

The system is designed to remain within the body of a patient as an implant for a predetermined therapeutically effective amount of time. Implantation can be temporary or permanent. The system can be non-absorbable, absorbable or resorbable, including any combinations of these material properties, depending on the desired treatment. For example, portions of the system may be constructed of a bioabsorbable material designed to last for a predetermined period of time within the patient. The general characteristics of the materials and design used in the system will withstand the various forces exerted upon it during implantation (for example, frictional forces associated with tissue resistance) and after implantation (for example, normal activities, including walking, running, coughing, sneezing, and other "normal" activities).

The system as disclosed can be anchored to a variety of locations in the body, including, but not limited to fascia, muscle, bone, ligament, and the like. In addition, an anchor can further comprise an adjustment device that permits the surgeon to adjust the tension on the suspension members either at the time of implantation, or post-implantation. The adjustment device can be a simple screw-like mechanism, around which an end of the suspension line is wrapped. Turning the screw in one direction increases the tension on the line, while turning in the opposite direction decreases tension. In some embodiments, the tensioner is adjusted through a small incision using an endoscope or other like instrument, in combination with a tool designed to turn the tensioner.

In some embodiments the suspension members can be anchored to a single attachment point. In some embodiments multiple attachment points are used. The elements of the devices can be elastic, or non-elastic as desired. In some embodiments, a braided portion overlying an elastomeric portion is used. In some embodiments, the braided portion is also elastomeric.

The skilled artisan will recognize the interchangeability of various features from different embodiments. Similarly, the various features and steps discussed above, as well as other known equivalents for each such feature or step, can be mixed and matched by one of ordinary skill in this art to perform compositions or methods in accordance with principles described herein. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein.

What is claimed is:

1. A system for use in supporting a tissue in a patient's body, comprising:
   a device, the device comprising:
      a support member, adapted to engage at least a portion of the tissue, the support member comprising a first end and a second end, the support member further comprising a plurality of support elements; and
      first and second suspension members, the first suspension member being coupled to the first end of the support member, the second suspension member being coupled to the second end of the support member;
      wherein at least one of the first and second suspension members is configured to be secured to a location in the patient's body;
      wherein the plurality of support elements is configured to distribute a load, from the tissue engaged by the support member, imposed on the support member; and wherein at least one of the first and second suspension members is configured to transmit a force through the support member, the force effective to move the engaged portion of the tissue from a first position to a second position; and a delivery system for delivering the device, wherein:
the delivery system comprises a first needle and a second needle, the first needle being configured to be coupled to the device and the second needle having a tubular body for slidably receiving the first needle;
the first needle has a first radius of curvature and the second needle has a second radius of curvature, the first radius of curvature being different from the second radius of curvature; and
the second needle is configured to adopt a new radius of curvature, wherein the new radius of curvature depends on how much of the first needle is held within the second needle.

2. The system of claim 1, wherein the first suspension member is coupled to each support element at a first end of each support element, and the second suspension member is coupled to each support element at a second end of each support element.

3. The system of claim 1, wherein the second position is superior to the first position.

4. The system of claim 1, wherein the second position is at least one of posterior, medial, and lateral, relative to the first position.

5. The system of claim 1, wherein the second position is posterior to the first position.

6. The system of claim 1, wherein each of the plurality of support elements is elongate and has a length extending along an arc, or line, that extends between the first end of the support member and the second end of the support member;
wherein a first of the plurality of support elements is spaced apart from a second of the plurality of support elements along at least about 10% of a length of the first of the plurality of support elements; and
wherein the length of the plurality of support elements extends from the first end of the support member to the second end of the support member.

7. The system of claim 1, wherein a first of the plurality of support elements is spaced apart from a second of the plurality of support elements along at least about 30% of a length of the first of the plurality of support elements; and
wherein the length of the plurality of support elements extends from the first end of the support member to the second end of the support member.

8. The system of claim 1, wherein at least one of the support elements is fusiform shaped.

9. The system of claim 1, wherein at least one suspension member is configured to be secured to at least one of muscle, fascia, bone, ligament, tendon, and skin.

10. The system of claim 1, wherein the portion of the tissue being engaged comprises at least one of breast tissue, buttock tissue, facial tissue, arm tissue, abdominal tissue, and leg tissue.

11. The system of claim 1, wherein each support element comprises at least one of an elongate member and a mesh.

12. The system of claim 1, wherein each of the plurality of support elements is coupled to a separator, effective to maintain spacing between adjacent support elements.

13. The system of claim 1, wherein the support member comprise an engagement member, effective to limit movement of the support member relative to the engaged portion of the tissue.

14. The system of claim 13, wherein the engagement member comprises at least one of a barb, a hook, and a suture.

15. The system of claim 1, wherein at least a portion of the device comprises a biodegradable material.

16. The system of claim 1, further comprising a coating effective to enhance at least one of biocompatibility and healing.

17. The system of claim 1, wherein the support member is made from a different material than the first and second suspension members.

18. The system of claim 1, wherein the support member comprises color coding to indicate regions of the support member that include support elements.

19. A device, for use in supporting a tissue in a patient's body, comprising:
a support member, adapted to engage at least a portion of the tissue, the support member comprising a first end and a second end, the support member further comprising a plurality of support elements;
first and second suspension members, the first suspension member being coupled to the first end of the support member, the second suspension member being coupled to the second end of the support member;
wherein at least one of the first and second suspension members is configured to be secured to a location in the patient's body;
wherein the plurality of support elements is configured to distribute a load, from the tissue engaged by the support member, imposed on the support member; and
wherein at least one of the first and second suspension members is configured to transmit a force through the support member, the force effective to move the engaged portion of the tissue from a first position to a second position; and
a linking device coupled to the first end of the support member, wherein the linking device comprises a tubular body configured to receive a received end, the received end being the second end of the same support member or an end of a different support member, to link the received end to the first end of the support member, and wherein the linking device further comprises a skived area near the first end of the tubular body.

* * * * *